US010078091B2

(12) United States Patent
DeBarber et al.

(10) Patent No.: US 10,078,091 B2
(45) Date of Patent: Sep. 18, 2018

(54) ANALYSIS OF A PANEL OF CEREBROTENDINOUS XANTHOMATOSIS BIOMARKERS USING SITE SPECIFIC DERIVATION AND LC/MS/MS WORKFLOW

(71) Applicants: DH Technologies Development Pte. Ltd., Singapore (SG); Oregon Health and Science University, Portland, OR (US)

(72) Inventors: Andrea DeBarber, Vancouver, WA (US); Subhasish Purkayastha, Acton, MA (US); Robert D. Steiner, Portland, MA (US); Michal Weinstock, Newton, MA (US)

(73) Assignees: DH Technologies Development Pte. Ltd., Singapore (SG); Oregon Health and Science University, Portland, OR (US)

( * ) Notice: Subject to any disclaimer, the term of this patent is extended or adjusted under 35 U.S.C. 154(b) by 406 days.

(21) Appl. No.: 14/401,427

(22) PCT Filed: May 17, 2013

(86) PCT No.: PCT/IB2013/000961
§ 371 (c)(1),
(2) Date: Nov. 14, 2014

(87) PCT Pub. No.: WO2013/171568
PCT Pub. Date: Nov. 21, 2013

(65) Prior Publication Data
US 2015/0323554 A1    Nov. 12, 2015

Related U.S. Application Data

(60) Provisional application No. 61/649,044, filed on May 18, 2012.

(51) Int. Cl.
G01N 33/00    (2006.01)
G01N 33/92    (2006.01)
(Continued)

(52) U.S. Cl.
CPC .............. *G01N 33/92* (2013.01); *G01N 33/58* (2013.01); *G01N 33/6848* (2013.01);
(Continued)

(58) Field of Classification Search
CPC ...................................................... G01N 33/92
(Continued)

(56) References Cited

U.S. PATENT DOCUMENTS 8,158,435 B2    4/2012  Debarber et al.
2010/0129923 A1*  5/2010  DeBarber .......... G01N 33/6893
                                                          436/128

(Continued)

OTHER PUBLICATIONS

International Search Report from International Patent Application No. PCT/IB2013/000961, dated Sep. 17, 2013.
(Continued)

*Primary Examiner* — Christine T Mui
*Assistant Examiner* — Emily R. Berkeley

(57) ABSTRACT

A method, a labeling reagent, sets of labeling reagents, and labeling techniques are provided for the analysis of ketosterol biomarkers such as bile acid precursors from human plasma, serum or whole blood. This method is used for new born screening for Cerebrotendinous Xanthomatosis (CTX). Methods for labeling, analyzing, and quantifying ketosterol biomarkers are also disclosed as are methods that also use mass spectrometry.

16 Claims, 16 Drawing Sheets

(51) Int. Cl.
*G01N 33/58* (2006.01)
*H01J 49/00* (2006.01)
*G01N 33/68* (2006.01)

(52) U.S. Cl.
CPC ...... *G01N 33/6893* (2013.01); *H01J 49/0031* (2013.01); *G01N 2333/90251* (2013.01); *G01N 2400/00* (2013.01); *G01N 2800/04* (2013.01); *G01N 2800/065* (2013.01); *G01N 2800/385* (2013.01)

(58) Field of Classification Search
USPC .......................................................... 436/173
See application file for complete search history.

(56) References Cited

U.S. PATENT DOCUMENTS

2010/0249082 A1* 9/2010 Hess .................... C07J 41/0016
514/175

2011/0003395 A1* 1/2011 Dey ........................ G01N 30/72
436/98
2011/0183420 A1 7/2011 Dey et al.

OTHER PUBLICATIONS

Debarber et al. ESI-MS/MS quantification of 7 α-hydroxy-4-cholesten-3-one facilite rapid, convenient diagnostic testing for cerebrotendinous xanthom atosis, Clinica Chimica Acta, 2010, vol. 411, Issue 1-2.

Matysik et al., Monitoring of 7 α-hydroxy-4-cholesten-3-one during therapy cerebrotendinous xanthomatosis: a case report, Chemistry and Physics of Lipids, 2011, vol. 164, Issue 6.

Honda et al., Highly sensitive analysis of sterol profiles in human serum by LC-ESI-MS/MS, Journal of Lipis Research, 2008, vol. 49.

DeBarber, Andrea E. et al, "A Blood test for Cerebrotendinous Xanthomatosis with Potential for Disease Detection in Newborns", Journal of Lipid Research, vol. 55, 2014, pp. 146-154.

* cited by examiner

| QAO-tagged Ketosterol | LOD underivatized in solvent (pg on-column) | LOD derivatized in solvent (pg on-column) | Enhancement factor after derivatization | LOD derivatized DCS serum (ng/mL) | Linearity in DCS serum $R^2$ | Dynamic range (ng/mL) | CV (%) at LOQ (n=5) | Accuracy (%) at LOQ (n=3) |
|---|---|---|---|---|---|---|---|---|
| 7αC4 | 19 | 0.04 | 475 | 0.65 | >0.998 | 1-4166 | 9.5 | ~80% |
| 4-Cholesten-3-one | 100 | 0.04 | 2500 | 0.65 | >0.996 | 1-4166 | 10.7 | NA |
| 5α-Cholestan-3-one | 22 | 0.08 | 275 | 1.00 | >0.995 | 1.2-4166 | 8.8 | NA |

FIG. 7

|  | n | within-run | | | between-run | | |
|---|---|---|---|---|---|---|---|
|  |  | Cal conc | Accuracy (%) | RSD (%) | Cal conc | Accuracy (%) | RSD (%) |
| 2.5 ng/mL | 3 | 1.6 | 63.2 | 9.9 | 3.5 | 142 | 28.2 |
| 5.0 ng/mL | 3 | 3.5 | 69.7 | 7.9 | 5.3 | 106 | 5.4 |
| 250 ng/mL | 3 | 262 | 105 | 1.7 | 254 | 102 | 1.5 |
| unaffected | 3 | 9.9 | - | 3.1 | 13.8 | - | 15.1 |
| CTX(25x dil) | 3 | 86.9 | - | 4.0 | 80.4 | - | 2.6 |

|  | n | within-run | | | between-run | | |
|---|---|---|---|---|---|---|---|
|  |  | Cal conc | Accuracy (%) | RSD (%) | Cal conc | Accuracy (%) | RSD (%) |
| 2.5 ng/mL | 3 | 1.5 | 58.4 | 10.6 | 2.7 | 110 | 35.2 |
| 5.0 ng/mL | 3 | 3.4 | 68.5 | 4.9 | 4.5 | 90 | 4.9 |
| 250 ng/mL | 3 | 242 | 96.8 | 0.4 | 250 | 100 | 2.6 |
| unaffected | 3 | 9.9 | - | 4.8 | 12.8 | - | 17.7 |
| CTX (25x dil) | 3 | 84.2 | - | 2.7 | 79.3 | - | 2.8 |

| | | within-run | | | between-run | | |
|---|---|---|---|---|---|---|---|
| | n | Cal conc | Accuracy (%) | RSD (%) | Cal conc | Accuracy (%) | RSD (%) |
| 2.5 ng/mL | 3 | 1.9 | 75.3 | 6.3 | 2.6 | 104 | 15.2 |
| 5.0 ng/mL | 3 | 4.2 | 83.5 | 5.7 | 4.8 | 95.7 | 1.4 |
| 250 ng/mL | 3 | 243 | 97.1 | 3.1 | 250 | 100 | 4.5 |
| unaffected | 3 | 0.3 | - | 38.2 | 0.7 | - | 93.1 |
| CTX(25x dil) | 3 | 145 | - | 0.7 | 104.2 | - | 4.1 |

| | 7αC4 (ng/ml) | 7α12αC4 (ng/ml) | cholestanol* (μg/ml) |
|---|---|---|---|
| Untreated CTX patients (n=xx) | 1174 ± 711 (204-1828) | 1545 ± 1141 (57-2420) | |
| Unaffected Individuals (n=xx) | 6.4 ± 5.3 (1.6-22) | 0.4 ± 0.27 (0.1-0.8) | ND |

Mean ± SD and (range of results) given
\* Determined from 50μl plasma
ND - not determined, normally <8-10μg/ml

ANALYSIS OF A PANEL OF CEREBROTENDINOUS XANTHOMATOSIS BIOMARKERS USING SITE SPECIFIC DERIVATION AND LC/MS/MS WORKFLOW

RELATED APPLICATIONS

This application claims the benefit of priority from U.S. Provisional Application Ser. No. 61/649,044, filed on May 18, 2012, the entire contents of which is incorporated by reference herein.

GOVERNMENT LICENSE RIGHTS

This invention may have been made in part with government support under OCTRI grant number 5KL2 RR024141-04 awarded by NCRR and the NCATS of the NIH. The government may have certain rights in the invention.

FIELD OF THE INVENTION

The teachings described herein relate to methods and kits directed to the analysis of ketosterol bile acid precursors using labeling reagents.

BACKGROUND

Newborn screening programs can be effective at saving lives as well as preventing serious morbidity, such as mental retardation, through the early detection and treatment of genetic conditions. Thus, screens for newborns should be expanded to include additional disorders, particularly those having treatment options.

Genetic conditions where a newborn screening program could be particularly useful include those involving alterations in sterol pathways. These conditions can cause untimely mortality and morbidity and include conditions such as cerebrotendinous xanthomatosis (CTX), Smith-Lemli-Opitz syndrome, familial hyper-cholesterolaemia, and congenital adrenal hyperplasia. CTX has been identified as a candidate for universal newborn screening in a recent American College of Medical Genetics report. However, to be effective, screening and/or diagnosis methods for CTX must have sufficient sensitivity and selectivity.

CTX is a rare genetic sterol condition caused by mutations in the CYP27A gene (the CYP27A gene is also known as sterol 27-hydroxylase gene). The CYP27A gene is associated with the P450 enzyme is important in production of bile acids. When CYP27A activity is inhibited or blocked, bile acid precursors will accumulate in various tissues. CTX often presents itself in childhood with the symptoms caused by the accumulation of the ketosterols bile acid precursors and their derivatives slowly increasing. Often CTX is not identified until adulthood after significant damage has been done. The biochemical phenotype of CTX is shown in FIG. 12.

Screening of biomarkers for 27-hydroxylase deficiencies has previously been considered. However, the biomarkers for CTX are ketosterol biomarker compounds and such screening presents a challenge because these biomarkers are generally present at low levels in clinical and biological samples such as plasma. Additionally, the biomarkers may be present at even lower levels in unaffected individuals, making it difficult to obtain a reference. The highly hydrophobic ketosteroids pose chromatographic challenge when using Reversed Phase (RP) chromatography. The detection and quantification of ketosterol biomarker steroids by mass analysis are also particularly challenging because of poor ionization efficiency of such compounds, complex ionization patterns, interference in the mass measurement by isobaric compounds and low sample concentrations in the sample medium.

Standard chromatographic techniques such as GC-MS methods for analysis after chemical derivatization are available. See, e.g., Song, J. et al., Journal of Chromatography B., Vol. 791, Issues 1-2, (127-135) 2003, the contents of which are incorporated by reference. Methods using fluorescence detection and some immunoassays, including radioimmunoassays (RIAs), are also available, but these usually do not offer multi-component analysis. The major problems with RIAs are lack of specificity and the need to perform a different assay for each steroid.

One existing analytical method to analyze ketosterols such as 5α-cholest-3-one and other bile acid precursors that accumulate in CTX and bowel disease has been described, for example, in U.S. Pat. No. 8,158,435, Andrea E. DeBarber, et. al.; Clinica Chimica Acta, 411 (2010) 43-48; Akira Honda, et. al.: The Journal of Biological Chemistry 276, 37 (2001) 34579-34585; and M. Camilleri et. al. Neurogastroenterol Motil (2009) 21,734-e43 Technical Note, herein incorporated by reference. GC-FID or GC-MS was used for the biochemical screening of CTX using Girard P derivatization with ESI-MSMS detection. However, limitations of GC based methodology include a lengthy analysis time (>30 min) and complex sample preparation.

The above challenges associated with detecting and quantifying ketosterol biomarker compounds in samples are magnified by the desire to rapidly screen and/or analyze a large number of biological samples for the specific compounds of interest or a panel of ketosterol bile acid precursors.

Additionally, conventional methods can be labor intensive and lack the requisite sensitivity to measure normal unaffected patient serum or whole blood samples, particularly for newborn screening, where typically only low sample volumes are available. It is hence desirable to have simple and specific methods for analyzing levels of CTX biomarkers in affected and normal human samples.

Thus, there remains a need for suitable sensitive and selective screening tests for identification and quantification of CTX. Such a test is preferably sensitive and specific for quantitation of ketosterols and other analytes that are useful as markers for CTX.

SUMMARY

In accordance with some broad aspects of the teachings, methods for detecting and quantifying CTX and IBS (irritable bowel syndrome) biomarkers in human samples, such as affected or normal human samples, are disclosed. In many embodiments, such methods employ quaternary aminoxy (QAO) reagents disclosed herein to improve the ionization efficiency of the analytes of interest, e.g., the CTX biomarkers, for their detection via mass spectroscopy to achieve the required LLOQ even for samples with a low volume, e.g., a sample volume less than about 5 microliters (μL), such as a sample volume of less than 10 μL. for example, in a range of about 3 to about 5 μL. Ketosterol bile acid precursors are examples of CTX and IBS biomarkers.

In various embodiments, isotopically enriched quaternary aminoxy reagents disclosed herein can be used to make internal standards for each analyte of interest by a simple reaction with a clean standard. In some embodiments, internal standards for a panel of biomarkers can be created by labeling known concentrations of a plurality of biomarkers analytes with isotopically variants of a quaternary aminoxy reagent disclosed herein (i.e., labeling each biomarker with a different isotopically variant of the QAO reagent). Such internal standards can be added to test samples to allow absolute quantifications of biomarkers of interest.

In various embodiments, the methods in accordance with the present teachings can be employed for highly sensitive and specific analysis of ketosterol biomarkers that allow for detection of the ketosteroid bile acid precursors from a variety of samples, including samples having a low volume and complex biological matrices.

In some embodiments, a method of diagnosing or screening for 27-hydroxylase deficiency is disclosed, which includes treating a human sample with a QAO reagent, such as those disclosed above, so as to label one or more ketosterol bile acid precursors in the sample, and subjecting the treated sample to LC-MS analysis to detect and quantify the labeled precursors.

In some cases, the above method can further include preparing one or more internal standards by labeling known concentrations of different ketosterol bile acid precursors with differently isotopically labeled QAO reagents disclosed herein. In some embodiments, such internal standards can be utilized for concurrently quantifying a panel of biomarkers using, e.g., LC-MS. For example, in some embodiments, the use of such internal standards allows for detecting and quantifying a panel of biomarkers in a single run of an LC-MS spectrometer.

In some embodiments, the quaternary aminoxy (QAO) reagent utilized for labeling ketosterol bile acid precursors for mass analysis include a labeling reagent of formula (I):

where n is 2, 3, 4, 5, or 6 and Y is:

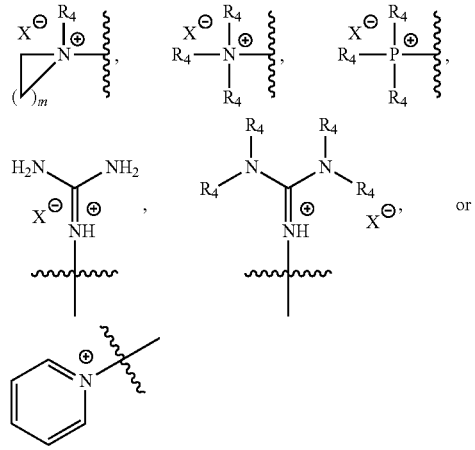

wherein each $R_4$ is independently H or a $C_1$-$C_{18}$ alkyl which is branched or straight chain,
m is an integer between 1 and 20, and
X is an anion,
or a salt or hydrate thereof.

In some embodiments, the labeling reagent is:

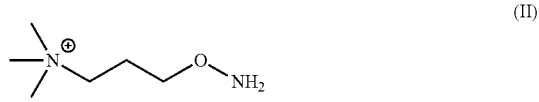

(II)

In some embodiments, the sample is a biological matrix, such as blood, serum, plasma, urine, or saliva. Analysis of a blood sample as part of a newborn screen is within the scope of the present teachings. For example, in some embodiments, the methods of the present teachings can be employed for analysis of dried blood, serum or plasma samples with volumes of 10 μL or less, or 5 μL or less or analysis of dried blood, serum or plasma sample obtained from a punch [of] a newborn screening card In some embodiments, 1, 2, 3, or 4 ketosterol bile acid precursors are analyzed, such as one or more of 7α-cholesten-3-one (7αC4), 5α-cholestan-3-one, 4-cholesten-3-one, 7α,12α-dihydroxy-4-cholesten-3-one, 7α-hydroxy-5β-cholestan-3-one, and 7α, 12α-dihydroxy-5β-cholestan-3-one (7α,12α-C4).

Further, the present invention provides for quantitation of masses at very low concentrations and thus can be used to measure the concentrations of ketosterol bile acid precursor, for example, in a population that does not have unusually high concentrations of these compounds.

In some embodiments, ketosteroid analysis kits can be provided to enable highly sensitive (low pg/mL concentrations) quantitation of ketosteroids from complex biological matrices.

In some embodiments, the methods described herein can measure relative concentration, absolute concentration, or both, and can be applied to one or more ketosterol bile acid precursors in one or more samples. The present methods can use an isotopically enriched Internal Standard (IS) or isobaric labeling reagents, as well as mass differential labeling reagents, depending on the selection of isotopic substitution and labeling strategies for the compounds for the detection of ketosteroids.

In some embodiments, the present teachings provide a method for quantifying ketosteroids and analytes containing keto or aldehyde functionality. In some embodiments, the method can comprise derivatization chemistry and a liquid chromatography/tandem mass spectrometry (LC/MSMS) workflow. The method can comprise using a permanently charged aminooxy reagent which can significantly increase the detection limits of ketosteroids.

These and other features of the embodiments as will be apparent are set forth and described herein.

BRIEF DESCRIPTION OF THE DRAWINGS

A detailed description of various embodiments is provided herein below with reference, by way of example, to the following drawings. The skilled person in the art will understand that the drawings, described below, are for illustration purposes only. The drawings are not intended to limit the scope of the applicant's teachings in any way.

FIG. 7 demonstrates QAO derivatization method performance for three different QAO-tagged ketosterols.

FIG. 11A is a chromatogram of a blank 7αC4 in DCS. FIG. 11B is an internal standard of 7αC4. FIG. 11C is a chromatogram of 2.5 ng/mL 7αC4. FIG. 11D is an internal standard of 7αC4. FIG. 11E is a chromatogram of a typical sample of 7αC4. FIG. 11F is an internal standard of 7αC4.

FIGS. 16B and 16C provide the CTX sample at 25-fold dilution.

FIGS. 24B and 24C provide the CTX sample with the d0 (upper trace) and d3 (lower trace).

Figure 1:
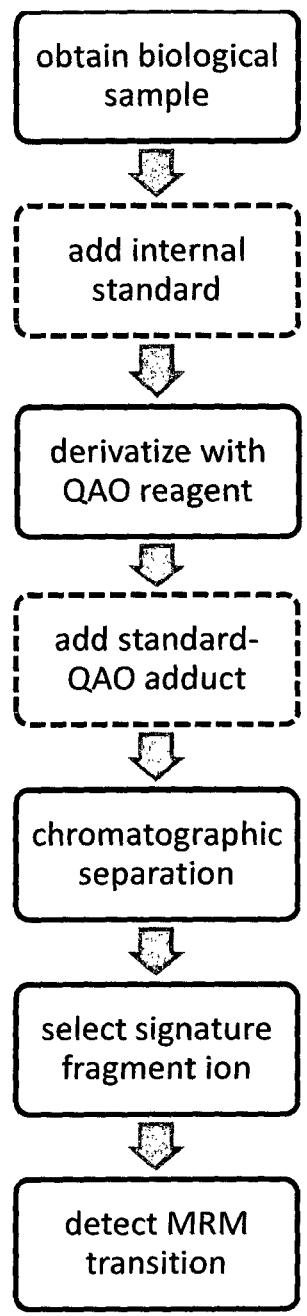
FIG. 1 is a flow diagram of a method showing sample preparation, derivatization, and LC/MS/MS analysis of the derivatized analyte.

It will be understood that the drawings are exemplary only and that all reference to the drawings is made for the purpose of illustration only, and is not intended to limit the scope of the embodiments described herein below in any way. For convenience, reference numerals may also be repeated (with or without an offset) throughout the figures to indicate analogous components or features.

DETAILED DESCRIPTION OF VARIOUS EMBODIMENTS

It will be appreciated that for clarity, the following discussion will explicate various aspects of embodiments of the teachings, but omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments may not require certain of the specifically described details in every implementation, which are set forth herein only to provide a thorough understanding of the embodiments. Similarly it will be apparent that the described embodiments may be susceptible to slight alteration or variation according to common general knowledge without departing from the scope of the disclosure. The following detailed description of embodiments is not to be regarded as limiting the scope of the present teachings in any manner.

This invention describes a method to detect and quantify ketosterol biomarkers such as bile acid precursors in a human sample, such as human plasma, serum or whole blood. In some embodiments, a method of diagnosis or screening for 27-hydroxylase (CYP27A1) deficiency, such as the CYP27A1 deficiency found in Cerebrotendinous Xanthomatosis (CTX) and irritable bowel syndrome (IBS) disorder is disclosed. In various embodiments, a fast and simple solution for simultaneous analysis of ketosterol biomarkers for CTX and irritable bowel syndrome disease is provided, thus offering the potential for routine screening for these disorders as well as other disorders and/or conditions associated with CYP27A1 deficiency. This can be useful, for example as a newborn screen for CTX.

Among the biomarkers of interest are 7α-cholesten-3-one (7αC4), 5α-cholestan-3-one, 4-cholesten-3-one, 7α,12α-dihydroxy-4-cholesten-3-one (7α12αC4), and other ketosterol bile acid precursors that are accumulated due to 27-hydroxylase (CYP27A1) deficiency.

It is useful and sometimes crucial to have a simple and inexpensive method to create internal standards for each ketosterol biomarker of interest. The QAO reagent as described herein substantially improves the ionization efficiency of these ketosterol bile acid precursors and provides significantly lower LLOQ than without the QAO reagent. This method provides for analysis using sample volume as low as 3-5 pL.

Embodiments as described herein include diagnosing or screening methods for newborn screens. However, the methods as described herein are equally useful for other populations and screening/diagnosis such as toddlers, and adults.

In some embodiments, isotopically enriched quaternary aminoxy reagent can be used to make IS for each analyte of interest by a simple reaction with a clean standard. A specific concentration of the internal standard of the panel of biomarkers can be created by labeling a known concentration of the analytes with the isotopic variant of the quaternary aminoxy reagent. This can then be spiked into the test sample and be used as an internal standard.

The ketosterol biomarkers used as analytes in the mass spectrometry techniques described herein are found in a variety of biological matrices such as physiological fluid samples, cell or tissue lysate samples, protein samples, cell culture samples, fermentation broth media samples, agricultural product samples, animal product samples, animal feed samples, samples of food or beverage for human consumption, combinations thereof, and the like, and essentially any sample where the ketosterol biomarker functionality is present. Examples of biological matrices comprise the physiological fluids, such as blood, serum, plasma, sweat, tears, urine, peritoneal fluid, lymph, vaginal secretion, semen, spinal fluid, ascetic fluid, saliva, sputum, breast exudates, and combinations thereof. In some embodiments, the samples are from a dried blood spot (DBS). In some embodiments, the DBS sample is a DBS from a neonatal screen.

The present teachings are applied to the ketosterol bile acid precursors that accumulate due to 27-hydroxylase (CYP27A1) deficiency. The ketosterol bile acid precursors include, for example, 7α-cholesten-3-one (7αC4), 5α-cholestan-3-one, 4-cholesten-3-one, and 7α,12α-dihydroxy-4-cholesten-3-one.

The present teachings are also applied to methods of screening and/or diagnosing CTX. Bile acid precursors particularly useful for the diagnosis and/or screening of CTX include 7α-cholesten-3-one (7αC4), 5α-cholestan-3-one, 4-cholesten-3-one, and 7α,12α-dihydroxy-4-cholesten-3-one.

Figure 9:
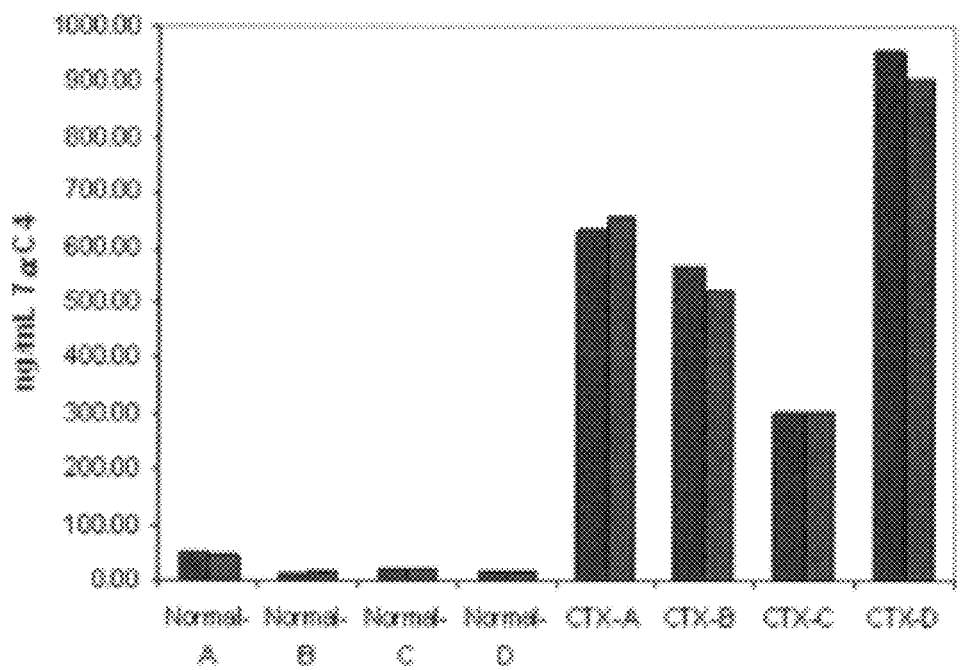
FIG. 9 is a graph showing the analysis of normal and CTX samples using d7 7αC4 as IS (right) and deuterated reagent as IS (left).

In some embodiments, there is provided a method of derivatizing an analyte comprising one or more bile acid precursors with a QAO reagent, ionizing the labeled analyte and detecting a signature ion fragment of said labeled analyte by mass analysis, and quantitating the concentration. In some embodiments, bile acid precursor comprises 7αC4 and a concentration of more than 50 ng/mL indicates CTX. In other embodiments, concentrations of 7αC4 of above 75 ng/mL, above 100 ng/mL, above 150 ng/mL, above 200 ng/mL, above 250 ng/mL, or above 300 ng/mL indicate CTX. In other embodiments, the concentration of a bile acid precursor that is used to define whether a sample is indicative of a 27-hydroxylase deficiency can be determined by using a table such as that provided in FIG. 9 for CTX-screening using 7αC4.

The present teachings are also applied to methods of screening and/or diagnosing Δ4-3-oxosteroid-5B reductase deficiency. Bile acid precursors particularly useful for the diagnosis and/or screening of Δ4-3-oxosteroid-5B reductase deficiency include 7α-cholesten-3-one and 7α,12α-dihydroxy-4-cholesten-3-one.

The present teachings are also applied to methods of screening and/or diagnosing irritable bowel syndrome (IBS).

The present teachings are also applied to methods of screening and/or diagnosing bile acid malabsorption. The bile acid precursors particularly useful for bile acid malabsorption include 7α-hydroxy-4-cholesten-3-one.

In some embodiments, a single ketosterol bile acid precursor is quantified. In some embodiments, two are more of the ketosterol bile acid precursors are quantified. In some embodiments, three or more of the ketosterol bile acid precursors that are accumulated due to 27-hydroxylase (CYP27A1) deficiency are quantified as a panel in a single assay In yet other embodiments, four or more ketosterol bile acid precursors are quantified in one panel. In some embodiments, at least one of 7α-cholesten-3-one (7αC4) and 7α,12α-dihydroxy-4-cholesten-3-one is quantified. In some embodiments, each of 7α-cholesten-3-one (7αC4), 5α-cholestan-3-one, 4-cholesten-3-one, and 7α,12α-dihydroxy-4-cholesten-3-one is quantified. In some embodiments, each of 7α-cholesten-3-one (7αC4), 5α-cholestan-3-one, 4-cholesten-3-one, 7α,12α-dihydroxy-4-cholesten-3-one, 7α-hydroxy-5β-cholestan-3-one, and 7α,12α-dihydroxy-5β-cholestan-3-one are analyzed. In some embodiments, each of 7α-cholesten-3-one (7αC4), 5α-cholestan-3-one, 4-cholesten-3-one, 7α,12α-dihydroxy-4-cholesten-3-one, 7α-hydroxy-5β-cholestan-3-one, and 7α,12α-dihydroxy-5β-cholestan-3-one is quantified.

The samples may be enriched by various methods. The enrichment method is dependent upon the type of sample, such as blood (fresh or dried), plasma, serum, urine, or saliva. Exemplary enrichment methods include protein precipitation, liquid-liquid extraction, solid-liquid extraction, and ultrafiltration. Other enrichment methods, or the combination of two or more enrichment methods may be used.

Labeling Reagent

Thus, there is provided herewith a method for mass analysis of a ketosterol bile acid precursor using a specific labeling reagent and selection of a signature ion fragment for analysis.

In some embodiments, there is provided labeling reagents and sets of labeling reagents for the relative quantitation, absolute quantitation, or both, of ketosterol bile acid precursors in biological samples including a labeling reagent which is an amine oxide having general formula (I):

$$Y—(CH_2)_n—O—NH_2 \qquad (I)$$

where n is 2, 3, 4, 5, or 6 and Y has the structure:

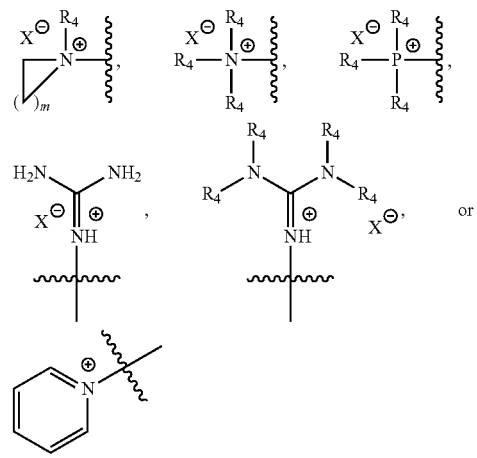

each $R_4$ is independently H or a $C_1$-$C_{18}$ alkyl which is branched or straight chain, m is an integer between 1 and 20, and X is an anion, or a salt or a hydrate thereof.

In some embodiments, n is 2-4 and in other embodiments, n is 3. In some embodiments, Y is $-N(CH_3)_3^{(+)}$. In some embodiments, m is an integer between 1 and 12 or an integer between 1 and 5. In some embodiments each $R_4$ is independently H or a $C_1$-$C_{12}$ alkyl which is branched or straight chain, or each $R_4$ is independently H or a $C_1$-$C_6$ alkyl which is branched or straight chain. In some embodiments, each $R_4$ is the same.

In some embodiments, the compound of formula (I) is a salt. In some embodiments, the salt is $CF_3COO-$; $CF_3CF_2COO-$; $CF_3CF_2CF_2COO-$; or $CF_3SO_3COO-$. In some embodiments, the salt is a perfluorocarboxylate salt.

In some embodiments, the labeling reagent of formula I is:

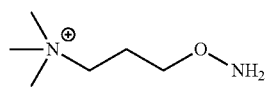

(II)

or a salt or hydrate thereof. In some embodiments, the compound of formula (II) is a salt. In some embodiments, the salt is $CF_3COO-$; $CF_3CF_2COO-$; $CF_3CF_2CF_2COO-$; or $CF_3SO_3COO-$. In some embodiments, the salt is a perfluorocarboxylate salt.

In various aspects, the present teachings provide labeled analytes, wherein the analyte can comprise at least one ketone group and the labeling reagent of formula (I) and/or (II). In various aspects, the present teachings provide labeled analytes, wherein the analyte can comprise at least one aldehyde group and the QAO labels described herein.

In various embodiments, the labeling reagents of formula (I) and/or (II) are used to label internal standards (IS). Such isotopically labeled internal standards can be particularly useful as isotopically labeled internal standards of many ketosteroids and other aldehyde compounds are not available commercially. Additionally, the standards that are available are often expensive and limited in form.

In some embodiments, the signature ion fragment of the ketosteroid bile acid precursor-QAO adduct comprises:

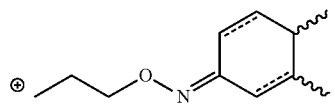

wherein each ═══ is either a single or double bond and each ∿∿ is either absent or indicates one or more bonds. When the analyte is 7α-cholesten-3-one (7αC4), the signature ion fragment can comprise, in some embodiments, a fragment ion having a mass of 152.0. When the analyte is 5α-cholestan-3-one, the signature ion fragment can comprise, in some embodiments, a fragment ion having a mass of 443.0. When the analyte is 4-cholesten-3-one, the signature ion fragment can comprise, in some embodiments, a fragment ion having a mass of 161.2.

The predominant signature ion fragment can be, for example, a neutral loss fragment or a neutral loss comprising a structural fragment of the analyte and the labeling reagent, or a part thereof. In some embodiments, there are more than one predominant signature ion fragments. In some embodiments, there are 2, 3, 4, or 5 predominant signature ion fragments.

Isotopically enriched Internal Standards (IS) for rare ketosterols such as those which are the ketosterol bile acid precursors are either not commercially available or very expensive to make. For example, while a stable isotope-labeled internal standard is available for 7αC4, there is no commercially-available labeled IS for any of 5α-cholestan-3-one, 4-cholesten-3-one, or 7α,12α-dihydroxy-4-cholesten-3-one.

Thus, in some embodiments, "heavy" (isotopically enriched) QAO reagent can provide internal standards for these ketosterols. In some embodiments, these internal standards are particularly advantageous if two or more ketosterol bile acid precursors are to be analyzed. Thus, isotopically enriched analogues of the labeling regent can be used and internal standards can be generated for quantitation. For example, heavy atom isotopes of carbon ($^{12}C$, $^{13}C$, and $^{14}C$), nitrogen ($^{14}N$ and $^{15}N$), oxygen ($^{16}O$ and $^{18}O$), sulfur ($^{32}S$, $^{33}S$, and $^{34}S$), and/or hydrogen (hydrogen, deuterium and tritium) can be used in the preparation of internal standards. United States Patent Application Publication No. US 2005/068446 A1 discloses synthesis of isotopically enriched compounds; mass analysis workflows and strategies are disclosed in U.S. Patent Application Publication No. US 2008/0014642 A1, both of which are incorporated herein in their entireties by reference.

The isotopically enriched compounds may comprise, for example:

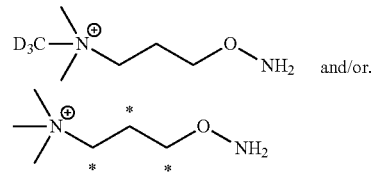

and/or.

The method can involve using an MRM workflow for quantitative analysis of ketosteroids. The reagents can be isotope-coded for quantitative analysis of an individual or of a panel of keto compounds. In studies involved ketosteroid profiling the MS/MS fragmentation can be targeted at low collision energies to produce predominantly the neutral loss signature ion from the aminooxy-derivatized product. The MRM transition can be the mass of the derivatized steroid in Q1 and the mass of the neutral loss fragment in Q3. The present teachings provide, in some embodiments, a process for significantly reducing background noise via derivatization, resulting in improved sensitivity and targeted selection of Q3 fragments resulting in improved specificity.

In some embodiments, a set of isotopically labeled internal standards of steroids such as 7αC4 are provided. This set can comprise two or more adducts that comprise a known concentration of a ketosteroid labeled with the quaternary amine oxide (QAO) reagent as described herein, wherein each of the two or more adducts have different isotopically enriched analogues.

In some aspects, the present teachings comprise reagents and methods using mass differential tags including sets of mass differential labels, where one or more labels of the set contains one or more heavy atom isotopes. A set of mass differential labels can also be provided by preparing labels with different overall mass and different primary reporter groups or mass balance groups, although not every member of a set of mass differential tags need to be isotopically enriched. The present reagents and methods enable analysis of ketosterol biomarker analytes in one or more samples using mass differential labels and parent-daughter ion transition monitoring (PDITM). The present teachings can be used for qualitative and quantitative analysis of such analytes using mass differential tagging reagents and mass spectrometry. The mass differential tags comprise, but are not limited to, non-isobaric isotope coded reagents. The present teachings further comprise reagents and methods for the absolute quantitation of ketosterol biomarker compounds with or without the use of an isotopically enriched standard compound.

In some embodiments, sets of mass differential labels of general formula (I) and/or (II) are provided. In various embodiments, sets of isobaric labels of general formula (I) in their unsalted and/or unhydrated form are provided. In various embodiments, the masses of the labels differ by less than about 0.05 AMU in the unsalted and/or unhydrated form. The sets of labels provided can comprise two or more compounds of the general formula (I) or (II) wherein one or more of the compounds in the set of labels contains one or more heavy atom isotopes. In various embodiments, the heavy atom isotopes are each independently $^{13}C$, $^{15}N$, $^{18}O$, $^{33}S$, or $^{34}S$.

The compounds of formula (I) or (II) can be provided in a wide variety of salt and hydrate forms including, but not limited to, a mono-TFA salt, a mono HCl salt, a bis-HCl salt, or a bis-TFA salt, or a hydrate thereof. Variations on formula (I) are disclosed in U.S. Pat. Publ. 2011/0003395 and WO2005/068446, both of which are specifically incorporated by reference and are generally referred to as iTRAQ® reagents.

According to various embodiments, isotopes can be used as balance groups or balance moieties, for example, isotopes of hydrogen, carbon, nitrogen, oxygen, sulfur, chlorine, bromine, and the like. Exemplary balance groups or moieties can also comprise those described, for example, in U.S. Patent Application Publications Nos. US 2004/0219685 A1, published Nov. 4, 2004, US 2004/0219686 A1, published Nov. 4, 2004, US 2004/0220412 A1, published Nov. 4, 2004, and US 2010/0112708 A1, published May 6, 2010, all of which are incorporated herein in their entireties by reference.

In various embodiments, the one or more of the compounds of the set of labels is isotopically enriched with two or more heavy atoms; three or more heavy atoms; and/or with four or more heavy atoms. In various embodiments, a set of labels of formula (I) are formed by incorporating heavy atom isotopes. In some embodiments, the isotopes are present in at least 80 percent isotopic purity, at least 93 percent isotopic purity, and/or at least 96 percent isotopic purity.

Alternatively or in addition to mass balance tags, isobaric tags can be used. When isotopically enriched isobaric tags are used, sets of isobaric labels may comprise one, or more heavy atom isotopes. A set of isobaric labels can have an identical or specifically defined range of aggregate masses but can have a primary reporter ion or charged analyte of a different measurable mass. A set of isobaric reagents enables both qualitative and quantitative analysis of ketosterol biomarker analyte compounds using mass spectroscopy. For example, isotopically enriched isobaric tags and parent-daughter ion transition monitoring (PDITM) can be employed to detect and quantify one or more ketosterol bile acid precursors in a sample such as a specific ketosteroid or group of ketosteroids.

In embodiments comprising sets of isobaric labels, the linker group portion can be referred to as a balance group. For example, in some embodiments, a set of four isobaric labels are added to a set of one or more analytes and combined to form a combined sample that is subjected to MS/MS analysis to fragment the labeled ketosterol bile acid precursor and produce 4 reporter ions of different mass or charged analytes. The labels can be made isobaric by an appropriate combination of heavy atom substitutions of a reporter group or mass balance group or portion thereof or a mass balance group alone or portion thereof.

The following is an exemplary set of quaternary-aminooxy mass differential reagents, according to various embodiments of the present teachings:

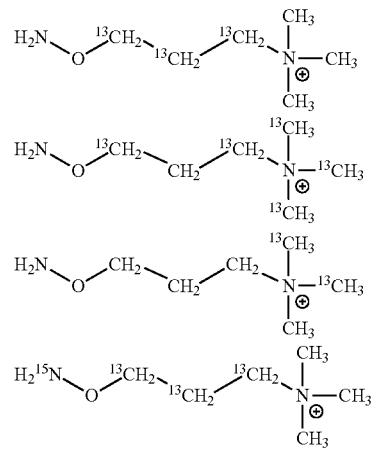

The following is an exemplary set of quaternary-aminooxy isobaric reagents, according to various embodiments of the present teachings:

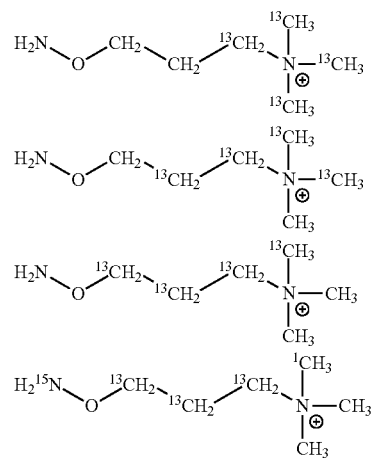

Analysis

The present teachings can provide reagents and methods for the analysis of one or more ketosterol bile acid precursor in one or more samples using mass differential labels, isobaric labels, or both, and parent-daughter ion transition monitoring (PDITM). The present teachings can provide methods for determining the relative concentration, absolute concentration, or both, of one or more analytes, such as ketosterol bile acid precursors, in one or more samples and provide methods whereby the relative concentration, absolute concentration, or both, of multiple analytes in a sample, one or more analytes in multiple samples, or combinations thereof, can be determined in a multiplex fashion using mass differential tagging reagents, isobaric tagging reagents, or both, and mass spectroscopy.

Some of the various methods as described herein can be explained by the flow diagram of FIG. 1. Particularly, a sample, which may be part a biological matrix such as blood, serum, or plasma can be selected and derivatized with one or more QAO labeling reagents disclosed herein by aminooxy chemistry followed by the mixing the labeled analyte and a QAO labeled standard. The mixture can be subjected to chromatographic separation, for example, by LC such as by HPLC, followed by mass analysis by MRM. If isotopically enriched reagent is used as an internal standard, it is preferably added after the derivatization step.

The method can also comprise the step of extracting the analyte using either liquid-liquid extraction, solid-liquid-extraction or protein precipitation using hydrophobic solvents prior to the derivatizing step. Alternatively a step of subjecting the analyte to chromatographic separation prior to the derivatizing step.

The signature fragment ion measured in the MRM can be carefully selected to comprise structural fragments with attached labeling reagent or part thereof. For example, where the labeling reagent includes a trimethyl amine, the signature fragment ion may include an ion which has lost the moiety $N(CH_3)_3$ as well as at least a portion of the backbone of the analyte. In some embodiments, the collision energy selected to form the signature fragment ion is a low collision energy so as to produce a single predominant signature fragment ion.

In some embodiments, the collision fragment energy is selected to be in the range of 10-130 eV. For example, 30 or 35 eV may be used.

In some embodiments, the analysis is done after minimal sample preparation. For example, sample preparation, starting from a dried blood spot is less than 30 minutes, or less than 20 minutes, or less than 10 minutes. In some embodiments, the analysis is done with no GC separation step performed during the preparation.

Several aspects provide for the reduction or elimination of background noise by using the derivatization chemistry of ketosteroids with permanently charged aminoxy reagent (Quaternary Aminoxy) and targeted fragmentation that can comprise both the reagent and the backbone of the derivatized compound. The derivatization with readily ionized/ionizable molecule can result in better ionization efficiency in, for example, ESI/MS/MS, which can increase the sensitivity and detection of the analytes of interest. When the fragment ion (Q3 signature ion) is carefully selected to comprise structural fragments with attached derivatization reagent (or part of the reagent), both the sensitivity and selectivity can be enhanced. The chances that a compound with the same Q1/Q3 transition would be detected and create BKG noise interference are very low.

With judicious selection of the signature ion fragment which comprises at least part of the readily ionizable labeling reagent, mass analysis can be done with significantly lower background noise and improved limits of detection and compared to MRM analysis of the ketosterol bile acid precursor performed without the addition of the labeling reagent. An enhancement factor as compared to the detection without derivatization may also be seen. For example, in some embodiments, where the limit of detection of an underivatized sample is between approximately 20 and 100 pg/mL on column, the limit of detection for a derivatized sample is less than about 0.08 pg/mL on column. Thus, an enhancement due to derivatization with the QAO is at least 200-fold, or at least 400-fold, or over 1000-fold, or over 2000-fold.

The linearity and dynamic range of the methods as provided herein may be particularly good. For example, in some embodiments, the linearity is greater than 0.990 in DSC. In some embodiments, the linearity is greater than 0.995 in DSC.

In some embodiments, the signature ion fragment is a neutral loss fragment that contains a portion of the analyte backbone and also contains a portion of the labeling reagent. In some embodiments, the signature ion fragment is one or more fragment having a m/z of 442.6, 93.3, 164.2, 152.1, 440.8, 456.8, 152.3, and/or 179.9. In these embodiments and in other embodiments, the signature ion fragment can be isotopically enriched, such as a $^{13}C$ enriched fragment.

Quantitation can be enabled by relative or absolute measurement of the signal derived from one or more analytes and standards. The positive charge can be transferred to the analyte which functions as the fragment ion to be detected by mass spectrometry.

Figure 2A:
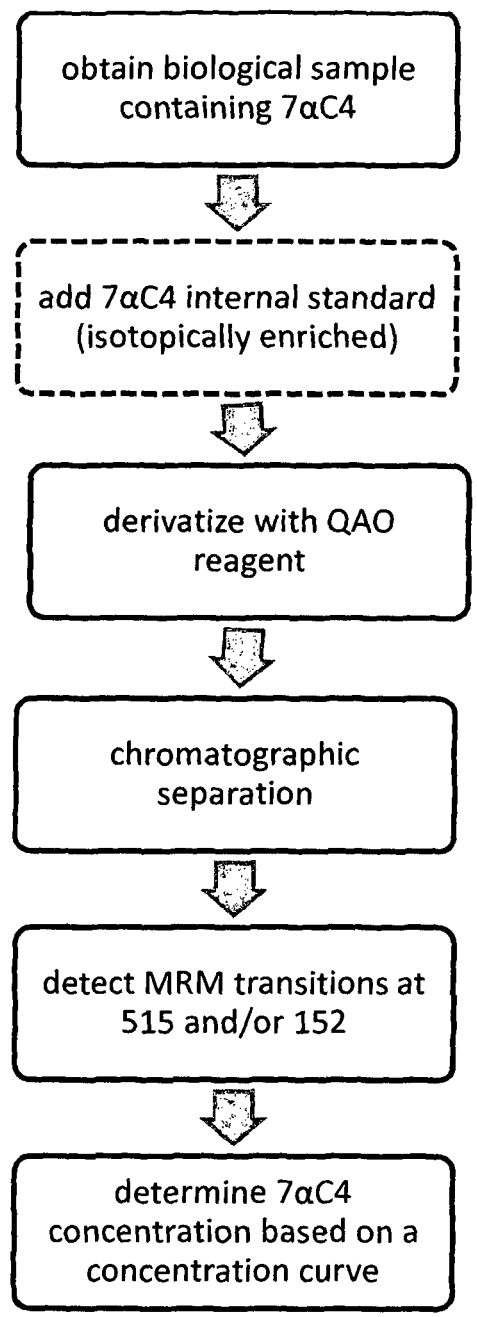
FIGS. 2A and 2B are flow diagrams of two method showing sample preparation, derivatization, and LC/MS/MS analysis of the derivatized analyte. 7αC4 is used as an example for each of FIGS. 2A and 2B.
Figure 2B:
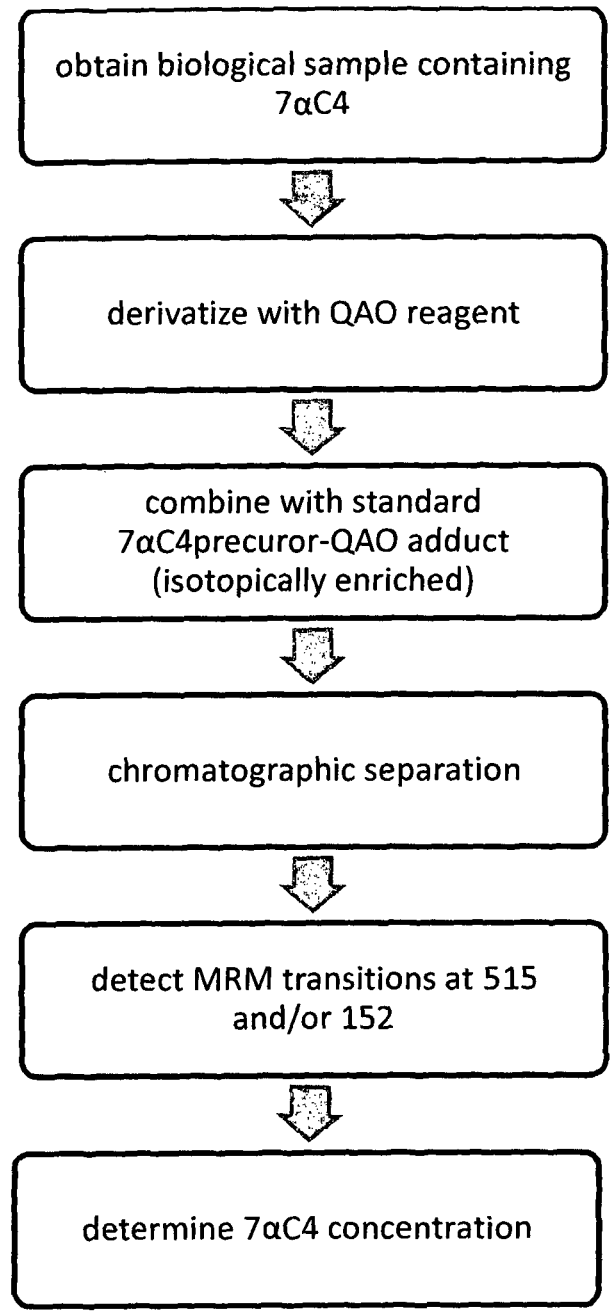

Other various methods as described herein can be explained by the flow diagrams of FIG. 2A, FIG. 2B, and FIG. 2C. Particularly, a sample containing a ketosterol bile acid precursor which is exemplified in these figures as 7αC4 and can be part a biological matrix such as blood, serum, or plasma, is selected. An internal 7αC4 standard, such as an isotopically enriched 7αC4 is optionally added to the sample. The 7αC4 can then be optionally extracted by, for example, liquid/liquid extraction or solid/liquid extraction. The sample and optionally the internal standard are derivatized with the QAO labeling reagent by aminooxy chemistry. In the method described in FIG. 2A, the adduct and an internal 7αC4 standard that has been isotopically enriched are derivatized. The sample is then derivatized with a QAO reagent by mixing and allowing the sample to incubate. In the method described in FIG. 2B, the adduct is labeled adduct combined with a 7αC4 standard that has been isotopically enriched. The sample is first derivatized with a QAO reagent by mixing and allowing the sample to incubate. It is then combined with a standard 7αC4 precursor-QAO adduct that has been isotopically enriched.

For the methods described in FIG. 2A and FIG. 2B, the mixture is subjected to chromatographic separation, for example, by LC such as by HPLC, followed by mass analysis by MRM, where the MRM transitions of one or more ketosterol bile acid precursors are analyzed. Quantitation is enabled by relative or absolute measurement of the signal(s) derived from one or more analytes and those of one or more standards. In FIG. 2A, the 7αC4 concentration is determined based on a concentration curve. The positive charge is transferred to the analyte which functions as the fragment ion to be detected by mass spectrometry.

Quantitation can be enabled by spiking increased amounts of known analytes concentrations into an endogenous-free matrix to create a calibration curve. The unknown concentrations of the samples are calculated from the linear regression of the concentration curve. The linear plot of the concentration curve comprises the concentration ratios of the calibrants and the internal standard versus the area ratios of the calibrants and the IS. Alternatively, relative quantitation can be enabled by a one point calibration using the known amounts of the spiked internal standards. For samples which are isobaric isomers, the chromatographic separation can be used to separate the samples prior to their mass analysis since these compounds may have the same mass patterns. Since isobaric ketosteroid in the biological sample may have a similar Q1/Q3 MRM transition, the isobaric ketosteroids can share the same fragmentation pattern with the analyte in order to appear as interference. In such cases, the isobaric ketosteroid is preferably chromatographically separated from the analyte.

An added advantage of the labeling reagent is that, in some embodiments, upon MSMS fragmentation, the derivatized analyte generates a fragment ion (Q3 signature ion) with the charge on the derivatized analyte which makes it amenable to MS3 analysis.

The derivatized analyte can enhance both the sensitivity and selectivity of the mass spectroscopic analysis. For example, the presently claimed methods may be used to detect a 3 ketosterol bile acid precursor from a biological matrix with a sensitivity that is 200 to 2000 times that of an underivatized sample. In some embodiments, the MS/MS sensitivity is enhanced 20 fold, 50 fold, 100 fold, 500 fold, 1000 fold, or even 2000 fold or more, depending on the compound. For example, in some embodiments, where the limit of detection of an underivatized sample is between approximately 20 and 100 pg/mL on column, the limit of detection for a derivatized sample is less than about 0.08 pg/mL on column. In some embodiments, the limit of detection after derivatization can be as low as <1 pg/mL. (See FIG. 7).

In various embodiments, the step of adding a label to a standard sample to label one or more of the standard compounds in the sample comprises a one step reaction where the aminooxy group forms an oxime with the ketone or aldehyde group of the analyte standard.

In various aspects, the present teachings provide methods for labeling a ketoanalyte to form a labeled analyte compound. In various embodiments, the methods comprise reacting a labeling compound of the general formula (I) or (II) with a ketone-containing compound. Specifically, the compounds 7α-cholesten-3-one (7αC4), 5α-cholestan-3-one, 4-cholesten-3-one, and 7α,12α-dihydroxy-4-cholesten-3-one were derivatized with the labeling reagent of formula I and specifically labeled in 5% acetic acid in MeOH for 60 minutes or more at room temperature.

Referring to the Examples, Figures, and Tables below, an example of labeling ketosterol bile acid precursors, with labeling reagents is shown. In these reactions, the aminooxy moiety reacts with the ketone or aldehyde on the steroid to form an oxime group on the labeled compound to yield a labeled analyte.

As described herein, methods for determining the concentration of one or more ketosterol bile acid precursors in two or more samples are provided by adding a different label to each sample, combining the differentially labeled samples and using PDITM to determine a concentration of one or more of the ketosterol bile acid precursor compounds in the samples. One of the samples may comprise a standard sample, such as a control sample, a reference sample, a sample with a compound of known concentration, etc. The methods can thus provide an analysis of multiple compounds from multiple samples.

In various embodiments, the step of determining the concentration of one or more labeled ketosterol bile acid precursors comprises determining the absolute concentration of one or more of the labeled ketosterol bile acid precursors, determining the relative concentration of one or more of the labeled ketone or analyte compounds, or combinations of both.

Certain methods comprise the steps of labeling one or more ketosterol bile acid precursors, in two or more samples of interest by adding to each sample of interest a different tag from a set of tags to form a panel of labeled ketosterol bile acid precursors. Each tag from the set of tags may comprise the labeling reagent or portion thereof as described herein. One or more of the labeled ketosterol bile acid precursors may be differentially labeled with respect to the sample from which each analyte was obtained or in which it is contained. The step of adding a label to a ketosterol bile acid precursor may comprise a one step reaction where a first portion of the label is comprised of the formula (I) or (II).

A portion of each of the samples can be combined to produce a combined sample and a portion thereof analyzed by parent-daughter ion transition monitoring and measuring the ion signal of one or more of the transmitted ions. The transmitted parent ion m/z range can comprise an m/z value of the labeled analyte compound and the transmitted daughter ion m/z range comprises an m/z value of a reporter ion derived to the tag of the labeled analyte compound or is the ionized analyte itself. The concentration of one or more of the labeled analyte compounds can then be determined based at least on a comparison of the measured ion signal of the corresponding transmitter reporter or analyte ions to one or more measured ion signals of a standard compound. The ion signal(s) can, for example, be based on the intensity (average, mean, maximum, etc.) of the ion peak, an area of the ion peak, or a combination thereof. One or more of the two or more samples of interest can be a standard sample containing one or more the standard compounds.

In some embodiments, the concentration of a ketosterol bile acid precursor is determined by comparing the measured ion signal of the corresponding labeled ketosterol bile acid precursor-reporter ion transition signal to one or more of:

(i) a concentration curve for a standard compound-reporter or analyte ion transition; or
(ii) a standard compound-reporter ion transition signal for a standard compound in the combined sample with the labeled ketosterol bile acid precursor.

In some embodiments, the "Parent-daughter ion transition monitoring" or "PDITM" is used as the method of analysis and workflow status. PDITM refers to a technique whereby the transmitted mass-to-charge (m/z) range of a first mass separator (often referred to as "MS" or the first dimension of mass spectrometry) is specifically selected to transmit a molecular ion (often referred to as "the parent ion" or "the precursor ion") to an ion fragmentor (e.g. a collision cell, photodissociation region, etc.) to produce fragment ions (often referred to as "daughter ions") and the transmitted m/z range of a second mass separator (often referred to as "MS/MS" or the second dimension of mass spectrometry) is selected to transmit one or more daughter ions to a detector which measures the daughter ion signal. This technique offers unique advantages when the detection of daughter ions in the spectrum is focused by "parking" the detector on the expected daughter ion mass. The combination of parent ion and daughter ion masses monitored can be referred to as the "parent-daughter ion transition" monitored. The daughter ion signal at the detector for a given parent ion-daughter ion combination monitored can be referred to as the "parent-daughter ion transition signal".

For example, one embodiment of parent-daughter ion transition monitoring is multiple reaction monitoring (MRM) (also referred to as selective reaction monitoring). In various embodiments of MRM, the monitoring of a given parent-daughter ion transition comprises using the first mass separator (e.g., a first quadrupole parked on the parent ion m/z of interest) to transmit the parent ion of interest and using the second mass separator (e.g., a second quadrupole parked on the daughter ion m/z of interest) to transmit one or more daughter ions of interest. In various embodiments, a PDITM can be performed by using the first mass separator (e.g., a quadrupole parked on a parent ion m/z of interest) to transmit parent ions and scanning the second mass separator over a m/z range including the m/z value of the one or more daughter ions of interest.

For example, a tandem mass spectrometer (MS/MS) instrument or, more generally, a multidimensional mass spectrometer instrument, can be used to perform PDITM, e.g., MRM. Examples of suitable mass analyzer systems comprise, but are not limited to, those that comprise one or more of a triple quadrupole, a quadrupole-linear ion trap, a quadrupole TOF, and a TOF-TOF.

Thus, PDITM can be performed on a mass analyzer system comprising a first mass separator, and ion fragmentor and a second mass separator. The transmitted parent ion m/z range of a PDITM scan (selected by the first mass separator) is selected to comprise a m/z value of one or more of the labeled analyte compounds and the transmitted daughter ion m/z range of a PDITM scan (selected by the second mass separator) is selected to comprise a m/z value of one or more of the reporter ions corresponding to the tag of the transmitted labeled analyte compound.

In some embodiments, parent daughter ion transition monitoring (PDITM) of the labeled analytes is performed using a triple quadrupole MS platform. More details about PDITM and its use are described in U.S. Patent Application Publication No. US 2006/0183238 A1, which is incorporated herein in its entirety by reference. In some embodiments, the aminooxy MS tagging reagent undergoes neutral loss during MSMS and leaves a reporter ion that is a charged analyte species. In some embodiments, the aminooxy MS tagging reagent forms a reporter ion that is a tag fragment during MSMS.

Thus, in various embodiments, for analyzing one or more ketosterol bile acid precursors in one or more samples using labels of the present teachings comprises the steps of: (a) labeling one or more ketosterol bile acid precursor compounds each with a different label from a set of labels of formula (II) providing labeled ketosterol bile acid precursor compounds, the labeled precursor compounds each having a mass balance or reporter ion portion; (b) combining at least a portion of each of the labeled analyte compounds to produce a combined sample; (c) subjecting at least a portion of the combined sample to parent-daughter ion transition monitoring; (d) measuring the ion signal of one or more of the transmitted analyte or reporter ions; and (e) determining the concentration of one or more of the labeled ketosterol bile acid precursors based at least on a comparison of the measured ion signal of the corresponding precursor or reporter ion to one or more measured ion signals of a standard compound. Accordingly, in various embodiments, the concentration of multiple ketosterol bile acid precursor compounds in one or more samples can be determined in a multiplex fashion, for example, by combining two or more labeled analyte compounds to produce a combined sample and subjecting the combined sample to PDITM, and monitoring the analyte or reporter ions of two or more of labeled precursor compounds.

The step of subjecting at least a portion of the combined sample to PDITM comprises loading the portion of the combined sample on a chromatographic column (e.g., a LC column, a gas chromatography (GC) column, or combinations thereof), subjecting at least a portion of the eluent from the chromatographic column to parent-daughter ion transition monitoring and measuring the ion signal of one or more of the transmitted reporter ions.

The one or more measured ion signals of a standard compound used in the step of determining the concentration of one or more of the labeled ketosterol bile acid precursor compounds can be provided in many ways. In various embodiments, one or more non-isotopically enriched standard compounds are labeled with a tag and at least a portion of one or more of the one or more labeled standard compounds is combined with at least a portion of each of the labeled precursor compounds to produce a combined sample; followed by subjecting at least a portion of this combined sample to PDITM and measuring the ion signal of one or more of the transmitted reporter ions.

A tag from the set of tags is added to one or more standard samples to provide one or more labeled standard samples, each standard sample containing one or more non-isotopically enriched standard compounds that are labeled by the tag, the tag added to the one or more standard samples being different from the tags added to the samples of interest. At least a portion of one or more of the one or more labeled standard samples is combined with at least a portion of each of the samples of interest to produce a combined sample; followed by subjecting at least a portion of this combined sample to PDITM and measuring the ion signal of one or more of the transmitted reporter ions.

The measured ion signals of one or more of the reporters or analyte ions corresponding to one or more of the one or more labeled standard compounds in the combined sample can then be used in determining the concentration of one or more of the labeled ketosterol bile acid precursor compounds and can be used to generate a concentration curve by plotting several values for standard compounds. Accordingly, in some embodiments, determining the concentration of a labeled analyte compound is based at least on a comparison of the measured ion signal of the corresponding reporter or analyte ions to the measured ion signal of one or more reporter or analyte ions corresponding to one or more of the one or more labeled standard compounds in the combined sample. The step of subjecting at least a portion of this combined sample to PDITM can comprise, e.g., a direct introduction into a mass analyzer system; first loading at least a portion of this combined sample on a chromatographic column followed by subjecting at least a portion of the eluent from the chromatographic column to PDITM and measuring the ion signal of one or more of the transmitted reporter ions.

As disclosed herein, PDITM on a standard compound can be performed on a mass analyzer system comprising a first mass separator, and ion fragmentor and a second mass separator. The transmitted parent ion m/z range of a PDITM scan (selected by the first mass separator) can be selected to comprise a m/z value of one or more of the labeled standard compounds and the transmitted daughter ion m/z range of a PDITM scan (selected by the second mass separator) can be selected to comprise a m/z value of one or more of the reporter or analyte ions corresponding to the transmitted standard compound.

Determining the concentration of one or more of the labeled analyte compounds can be based on both: (i) a comparison of the measured ion signal of the corresponding reporter or analyte ion to the measured ion signal of one or more reporter or analyte ions corresponding to one or more concentration curves of one or more standard compounds, and (ii) a comparison of the measured ion signal of the corresponding reporter ion to the measured ion signal of one or more reporter ions corresponding to one or more labeled standard compounds combined with the labeled ketosterol bile acid precursor. A non-isotopically enriched standard compound can be provided having a first concentration and labeled with a tag from the set of tags is combined with at least a portion of each of the labeled samples to produce a combined sample, and this combined sample can then be further analyzed as described herein.

In various embodiments of the present teachings, a concentration curve of a standard compound can be generated by: (a) providing an isotopically or non-isotopically enriched standard ketosterol bile acid precursor having a first concentration; (b) labeling the standard compound with a label from a set of labels wherein the labeled ketosterol bile acid precursor standard compound has a reporter ion portion; (c) loading at least a portion of the labeled standard compound on a chromatographic column; (d) subjecting at least a portion of the eluent from the chromatographic column to parent-daughter ion transition monitoring; (e) measuring the ion signal of the transmitted analyte or reporter ions; (f) repeating steps (a)-(e) for one or more different standard compound concentrations; and (g) generating a concentration curve for the standard compound based at least on the measured ion signal of the transmitted analyte or reporter ions at one or more standard compound concentrations.

In various embodiments, the present disclosure provides methods for determining the concentration of one or more ketosterol bile acid precursor in one or more samples. The methods comprise the steps of labeling each of one or more ketosterol bile acid precursors with a different tag from a set of tags of formula (I), where the Y group, which may be a quaternary nitrogen, comprises a reporter ion portion. The methods also comprises the step of combining at least a portion of each of the labeled precursor compounds to produce a combined sample and subjecting at least a portion of the combined sample to parent-daughter ion transition monitoring (where the transmitted parent ion m/z range comprises a m/z value of the labeled analyte compound and the transmitted daughter ion m/z range comprises a m/z value of a reporter ion corresponding to the tag of the labeled analyte compound) and measuring the ion signal of one or more of the transmitted reporter ions; then determining the concentration of one or more of the labeled analyte compounds based at least on a comparison of the measured ion signal of the corresponding reporter ion to one or more measured ion signals of a standard compound. The ion signal(s) can, for example, be based on the intensity (average, mean, maximum, etc.) of the ion peak, an area of the ion peak, or a combination thereof.

PDITM can be performed on any suitable mass analyzer known in the art, including a mass analyzer system comprising a first mass separator, and ion fragmentor and a second mass separator. The transmitted parent ion m/z range of a PDITM scan (selected by the first mass separator) is selected to comprise a m/z value of one or more of the labeled analyte compounds and the transmitted daughter ion m/z range of a PDITM scan (selected by the second mass separator) is selected to comprise a m/z value one or more of the reporter ions corresponding to the tag of the transmitted labeled analyte compound.

In some embodiments, the one or more ketosterol bile acid precursor samples are labeled with one or more of tags selected from a set of mass differential tags so that within the same experimental measurement: (i) multiple ketosterol bile acid precursor-containing compounds from different samples (e.g., a control, treated) can be compared and/or quantified; (ii) multiple concentration measurements can be determined on the same ketosterol bile acid precursor compound from the same sample; and (iii) different isolates of a clinical sample can be evaluated against a baseline sample.

The step of subjecting at least a portion of the combined sample to PDITM comprises introducing the combined sample directly into a mass analyzer system, e.g., by introduction of the combined sample in a suitable solution using an electrospray ionization (ESI) ion source.

The measured ion signals of one or more of the reporter ions corresponding to one or more of the one or more labeled standard compounds in the combined sample determines the concentration of one or more of the labeled analyte compounds. Determining the concentration of a labeled analyte compound is based at least on a comparison of the measured ion signal of the corresponding fragment ion to the measured ion signal of one or more fragment ions corresponding to one or more of the one or more labeled standard compounds in the combined sample. The step of subjecting at least a portion of this combined sample to PDITM can comprise, e.g., a direct introduction into a mass analyzer system; first loading at least a portion of this combined sample on a chromatographic column followed by subjecting at least a portion of the eluent from the chromatographic column to PDITM and measuring the ion signal of one or more of the transmitted reporter or analyte ions; or combinations thereof.

In some embodiments, determining the concentration of one or more of the labeled ketosterol bile acid precursor compounds comprises a comparison of the measured ion signal of the corresponding analyte or reporter ion to the measured ion signal of one or more reporter ions corresponding to one or more concentration curves of one or more standard compounds. A non-isotopically enriched standard compound is provided having a first concentration and labeled with a tag from a set of tags. A portion of the labeled standard compound is subjected to parent-daughter ion transition monitoring (where the transmitted parent ion m/z range comprises a m/z value of the labeled standard compound and the transmitted daughter ion m/z range comprises a m/z value of a reporter or analyte ion corresponding to the tag of the labeled standard compound) and the ion signal of the reporter or analyte ion is measured. The steps of labeling and the steps of PDITM and measuring the ion signal of the transmitted reporter or analyte ions are repeated for at least one more standard compound concentration different from the first concentration to generate a concentration curve for the standard compound.

Derivatization of the sample can be a one-step reaction where the QAO reagent comprises an aminooxy MS tagging portion as well as labeling portion as shown in general formula (I), or can be a multi-step reaction, where the adduct is formed by the reaction of oxo-containing reagent and the ketosterols bile acid precursor followed by combination with an aminooxy MS tag. These methods are described in U.S. Pat. Application Ser. No. 61/588,902, herein incorporated by reference. In some embodiments, the two-step labeling reaction can be provided that provides multi-plexing capability. For example, in some embodiments, different ketosterol bile acid precursors can be labeled with different QAO reagents. In other embodiments, different ketosterol bile acid precursors can be labeled with a single QAO reagent and the resulting adducts can be reacted with different aminoxy tags.

The method can further comprise providing a standard comprising a known ketosterol bile acid precursor, treating the known ketosterol bile acid precursor of the standard with a QAO reagent to form a standard adduct. In various embodiments, the standard can be treated with a QAO reagent via a one-step or two-step labeling reaction according to the present teachings to form a standard adduct. The standard adduct can then be mixed with an adduct formed by labeling a ketosterol bile acid precursor with a QAO reagent to form a mixture. The mixture can then be analyzed using mass spectrometry, e.g., using LC/MSMS spectrometry. In some embodiments, a relative concentration of a ketosterol bile acid precursor can be obtained. In other embodiments, absolute quantitation of a ketosterol bile acid precursor can be obtained by using a known concentration of a standard.

According to various embodiments, a method for relative quantitation of one or more ketosterol bile acid precursors can comprise labeling the one or more ketosterol bile acid precursor, followed by analysis using mass spectrometry. According to some embodiments the one or more ketosterol bile acid precursors and/or metabolites thereof can be quantified. According to some embodiments, the aminoxy tagging agents can comprise a set of isobaric tags. According to some embodiments, in a first step, at least one ketosterol bile acid precursor in a standard can be labeled with a QAO reagent to form a standard adduct. In a second step, the standard adduct can be tagged with a first isobaric tag from a set of isobaric tags. A test sample can be reacted with a QAO reagent to label one or more ketosterol bile acid precursors, if any, in the test sample. The labeled ketosterol bile acid precursors in the test sample can then be tagged with a second isobaric tag from the same set of isobaric tags, which is different from the first isobaric tag. The labeled standard and the labeled test sample can then be combined and the resulting mixture can be subjected to liquid chromatography (LC) separation on a reversed phase column. The labeled ketosterol bile acid precursors can have distinct retention times and can elute from the column at separate times. The eluting peaks can comprise peaks containing the labeled analyte and peaks containing the labeled standard. The eluent from the column can subsequently be analyzed using mass spectrometry.

It should be understood that absolute quantitation of ketosterol bile acid precursors, where the standard has a known concentration of a ketosterol bile acid precursor, can be performed in the same manner as described above for relative quantitation. Also, where ketosterol bile acid precursors and/or metabolites of ketosterol bile acid precursors are mentioned above, it should be understood that any ketosterol bile acid precursor can be used.

According to various embodiments, a sample comprising a plurality of different ketosterol bile acid precursors can be treated with different QAO reagents to label each of two or more of the ketosterol bile acid precursors with a different one of said reagents. The labeled sample can then be analyzed using mass spectrometry, e.g., LC/MSMS, to quantitate the labeled ketosterol bile acid precursors. In some embodiments, such analysis of the sample can be performed in a single run of the spectrometer. As discussed above, in some embodiments, the ketosterol bile acid precursors can be steroid or steroid-like analytes.

According to various embodiments, samples containing one or more compounds may be enriched by various methods prior to analysis. The enrichment method can depend upon the type of sample, such as blood (fresh or dried), plasma, serum, etc. Exemplary enrichment methods can comprise, without limitation, protein precipitation, liquid-liquid extraction, solid-liquid extraction, and ultrafiltration. Other enrichment methods, or a combination of two or more enrichment methods may be used.

In some embodiments, the analysis of ketosterol bile acid precursors can comprise generating reporter ions, e.g., via a high-energy collision in a mass spectrometer, and utilizing the intensity or the peak area of the reporter ions for quantitation. By way of example, the QAO reagents shown above can undergo neutral loss during high energy collisions (MSMS) leaving a charged analyte species as the reporter ion, and the reporter ion can then be subjected to $MS^3$ analysis. In some embodiments, the QAO reagents can generate a tag fragment upon a high energy collision, and the tag fragment can then be subjected to $MS^3$ analysis.

According to various embodiments, a plurality of mass spectrometry (MS) tagging agents can be used for labeling one or more ketosterol bile acid precursors and/or adducts thereof formed in accordance with the present teachings. According to some embodiments, the aminoxy tagging agents can fragment well to provide intense reporter ions. According to some embodiments, the aminoxy tagging agents can comprise tagging agents that are specifically designed for mass spectrometry and according to some embodiments, the aminoxy tagging agent is specifically designed for a Multiple Reaction Monitoring (MRM) assay. In some embodiments, an aminoxy tagging agent can be used to tag an adduct generated by labeling a ketosterol bile acid precursor. In some embodiments in which a standard adduct is used for quantitation of ketosterol bile acid precursors, an aminoxy tagging agent can be used to tag the standard adduct. In various embodiments, the standard adduct can be used for relative quantitation of ketosterol bile acid precursors. In some embodiments, where the concentration of the standard adduct is known, the standard adduct can be used for absolute quantitation of ketosterol bile acid precursor. In some embodiments, various aminoxy MS tagging agents can be used to label various analytes. For example, the aminoxy MS tagging agents can be different isobaric tags or different mass differential tags. By way of example, the aminoxy MS tagging agent used to tag the standard adduct can comprise a first isobaric tag from a set of isobaric tags, while the aminoxy MS tagging agent used to tag the adduct from the sample can comprise a second isobaric tag from the same set of isobaric tags, but that differs from the first isobaric tag.

Isobaric tags allow for multiplexing and provide a method for multiplexed analysis of ketosterol bile acid precursors, with high throughput and lower cost of analysis per sample. Since there is one common functional group in all of the ketosterol bile acid precursors, in various embodiments, only one tag is needed for each analyte. In some embodiments, using PDITM increases specificity and reduces the risk of error. The reagent design makes it a good tool for FlashQuant™ application and enables $MS^3$ capability which helps in confirming the identity of the analyte.

According to various embodiments, a first isobaric tag from one set of isobaric reagents can be made to contact a standard that can comprise a known ketosterol bile acid precursor, for example, at a known concentration. The contact can be made under conditions that favor a reaction between the first isobaric tag and the standard. A second isobaric tag from the same set of isobaric reagents as the first isobaric tag can be made to contact a sample comprising an unknown concentration of a ketosterol bile acid precursor. As described further below, the tagged analytes of the standard and sample can be mixed together and analyzed to determine the concentration of the analytes in the sample. The analysis can comprise separating the mixture to form separated analytes, and analyzing the separated analytes. Methods of separation that can be used include gas chromatographic methods, liquid chromatographic methods, other chromatographic methods, electrophoretic methods, electroosmotic methods, mass differential separation methods, and the like. In an exemplary embodiment, liquid chromatography is used to separate the various analytes in the mixture and thus form separated analytes.

In some embodiments, chromatographic separation can be performed on a reversed phase column and peaks eluting from the column can be subjected to subsequent analysis. In some embodiments, the subsequent analysis can comprise mass spectrometry or, more particularly, Parent Daughter Ion Transition Monitoring (PDITM). By comparing the results from the PDITM, the concentration of the ketosterol bile acid precursor in the sample can be determined, as is described in more detail below. More details about PDITM and its use can be found in published application US 2006/0183238 A1, which is incorporated herein in its entirety by reference.

According to some embodiments, mass differential tagging agents instead of isobaric tagging reagents, can be used, such as the mass differential agent pairs as described hereinabove. According to various embodiments, the aminoxy MS tagging agents can be used for relative and absolute quantitation in multiplex assays. According to some embodiments, the aminoxy MS tagging agents can be used for two-plex, three-plex, four-plex, and other multi-plex assays.

In some embodiments, the QAO reagent is combined with the sample at an equimolar concentration of oxo moieties. In some embodiments, an excess (for example, about 10%, about 20%, about a two-fold excess, or about a four-fold excess) of QAO reagent is added. In some embodiments less than an equimolar concentration of QAO is used, for example, the QAO concentration may be about 25%, about 50%, or about 75% of the molar concentration of the oxo moiety. In some embodiments, the QAO reagent is combined with the sample at a concentration of between 1 µg/mL-100 mg/mL, or between 100 µg/mL-10 mg/mL in the sample solution.

Different liquid chromatography and mass spectrometry methods, systems, and software that can be used in accordance with various embodiments of the present teachings include those described in U.S. Provisional Patent Application No. 61/182,748 filed May 31, 2009, and in U.S. Patent Application No. US 2006/0183238 A1 which published on Aug. 17, 2006. Both of these references are incorporated herein by reference.

According to yet other embodiments of the present teachings, a kit is provided that comprises a QAO reagent, such as those discussed above. In other embodiments, a kit is provided that comprises a QAO reagent and one or more aminoxy MS tagging agents. The aminoxy MS tagging agent can comprise compounds from the first and/or second category or set of aminoxy MS tagging agents, described above. In some embodiments, the kit can comprise a standard comprising a known ketosterol bile acid precursor.

According to various embodiments of the present teachings, a kit is provided that can comprise one or more of a QAO reagent and an aminoxy MS tagging agent. In some embodiments, the kit can comprise a standard containing a known concentration of a steroid analyte comprising a ketone.

In some embodiments, the kit can comprise at least one standard comprising a known concentration of a known ketosterol bile acid precursor. According to some embodiments, the aminoxy MS tagging agent can be an isobaric tag from a set of isobaric tags and in some embodiments the kit can include a plurality of different isobaric tags from a set of isobaric tags. According to some embodiments, the aminoxy MS tagging agent can be a mass differential tag from a set of mass differential tags and in some embodiments the kit can include a plurality of different mass differential tags from a set of mass differential tags. According to some embodiments, the kit can comprise a QAO reagent, an aminoxy MS tagging agent, a standard comprising a known ketosterol bile acid precursor and/or a known concentration of a known ketosterol bile acid precursor, and further can comprise instructions for labeling.

In some embodiments, a kit including one or more of the aminooxy reagents described herein can be provided, for example, comprising one or more permanently charged aminooxy compounds of formula (I) or (II).

In some embodiments, the method can comprise using an MRM workflow for quantitative analysis of ketosteroids. The reagents can be isotope-coded for quantitative analysis of an individual or of a panel of keto compounds. For profiling studies with the MS/MS fragmentation at low collision energies can result in one predominant signature ion. The signature ion can result from a neutral loss from the aminooxy derivatized product. The MRM transition can be the mass of the derivatized steroid in Q1 and the mass of the neutral loss fragment in Q3. For low concentrations quantitation, the MS/MS fragmentation at higher collision energy that include the labeling reagent and part of the backbone of the molecule can provide a process for significantly reducing background noise via derivatization, resulting in improved sensitivity and targeted selection of Q3 fragments resulting in improved specificity.

According to various embodiments, the present teachings provide a method that reduces or eliminates background noise without the problems associated with multistep cleanup of a biological sample and chromatographic separation. In some embodiments, the method eliminates background noise by utilizing a derivatization chemistry of ketosteroids with permanently charged aminooxy reagents (QAO) and targeted fragmentation that comprises both the reagent and the backbone of the derivatized steroid. The derivatization with a readily ionized/ionizable molecule results in better ionization efficiency in ESI MS/MS which increases sensitivity to the analyte. When the fragment ion that is the Q3 signature ion is selected to comprise structural fragments with an attached derivatization reagent, or a part of the reagent, both the sensitivity and selectivity can be enhanced. The chances that a compound with exactly the same Q1/Q3 transition would be detected and create background noise interference are very low. The only possibility for a similar Q1/Q3 MRM transition would be the existence of an isobaric ketosteroid in the biological sample. The isobaric ketosteroid would have to share the same fragmentation pattern with the analyte in order to appear as interference. In such a rare scenario, the isobaric ketosteroid can be chromatographically separated from the analyte.

According to various embodiments, an added advantage of the reagent design is that on MS/MS fragmentation the reagent generates a fragment ion, that is, a Q3 signature ion, with a charge on the derivatized analyte, making it amenable to $MS^3$ analysis. In some embodiments, the method can be implemented on classes of molecules with keto- or aldehyde functionality, the detection of which can benefit from derivatization for ultra high sensitivity analysis by MS/MS.

In some embodiments, after detecting the ketosterol bile acid precursor, the relative concentration of the ketosterol bile acid precursor is measured by comparison to that of a standard compound or by using a standard concentration curve. In some embodiments, the absolute concentration of at least one analyte is determined. In some embodiments, a calibrant comprising a standard labeled with at least one heavy atom is used. In some embodiments, the calibrant is a compound having at least two deuterium atoms.

The present teachings provide a highly sensitive and specific analysis of ketosteroids and classes of molecules containing a keto functionality. The present teachings provide higher signal to noise ratios with very low background noise in MS/MS due to, for example, careful deletion of signature ions to include part of the labeling reagent and part of the backbone of the molecule.

Mass Analyzers

A wide variety of mass analyzer systems can be used in the present teachings to perform PDITM. Suitable mass analyzer systems comprise two mass separators with an ion fragmentor disposed in the ion flight path between the two mass separators. Examples of suitable mass separators include, but are not limited to, quadrupoles, RF multipoles, ion traps, time-of-flight (TOF), and TOF in conjunction with a timed ion selector. Suitable ion fragmentors include, but are not limited to, those operating on the principles of: collision induced dissociation (CID, also referred to as collisionally assisted dissociation (CAD)), photoinduced dissociation (PID), surface induced dissociation (SID), post source decay, by interaction with an electron beam (e.g., electron induced dissociation (EID), electron capture dissociation (ECD)), interaction with thermal radiation (e.g., thermal/black body infrared radiative dissociation (BIRD)), post source decay, or combinations thereof.

Examples of suitable mass spectrometry systems for the mass analyzer include, but are not limited to, those which comprise one or more of a triple quadrupole, a quadrupole-linear ion trap (e.g., 4000 Q TRAP® LC/MS/MS System, Q TRAP® LC/MS/MS System), a quadrupole TOF (e.g., QSTAR® LC/MS/MS System), and a TOF-TOF.

In various embodiments, the mass analyzer system comprises a MALDI ion source. In various embodiments, at least a portion of the combined sample is mixed with a MALDI matrix material and subjected to parent-daughter ion transition monitoring using a mass analyzer with a MALDI ionization source. In various embodiments, at least a portion of the combined sample loaded on chromatographic column and at least a portion of the eluent mixed with a MALDI matrix material and subjected to parent-daughter ion transition monitoring using a mass analyzer with a MALDI ionization source.

The mass spectrometer system can comprise a triple quadrupole mass spectrometer for selecting a parent ion and detecting fragment daughter ions thereof. In this embodiment, the first quadrupole selects the parent ion. The second quadrupole is maintained at a sufficiently high pressure and voltage so that multiple low energy collisions occur causing some of the parent ions to fragment. The third quadrupole is selected to transmit the selected daughter ion to a detector. In various embodiments, a triple quadrupole mass spectrometer can comprise an ion trap disposed between the ion source and the triple quadrupoles. The ion trap can be set to collect ions (e.g., all ions, ions with specific m/z ranges, etc.) and after a full time, transmit the selected ions to the first quadrupole by pulsing an end electrode to permit the selected ions to exit the ion trap. Desired fill times can be determined, e.g., based on the number of ions, charge density within the ion trap, the time between elution of different signature peptides, duty cycle, decay rates of excited state species or multiply charged ions, or combinations thereof.

One or more of the quadrupoles in a triple quadrupole mass spectrometer can be configurable as a linear ion trap (e.g., by the addition of end electrodes to provide a substantially elongate cylindrical trapping volume within the quadrupole). In various embodiments, the first quadrupole selects the parent ion. The second quadrupole is maintained at a sufficiently high collision gas pressure and voltage so that multiple low energy collisions occur causing some of the parent ions to fragment. The third quadrupole is selected to trap fragment ions and, after a fill time, transmit the selected daughter ion to a detector by pulsing an end electrode to permit the selected daughter ion to exit the ion trap. Desired fill times can be determined, e.g., based on the number of fragment ions, charge density within the ion trap, the time between elution of different signature peptides, duty cycle, decay rates of excited state species or multiply charged ions, or combinations thereof.

The mass spectrometer system can comprise two quadrupole mass separators and a TOF mass spectrometer for selecting a parent ion and detecting fragment daughter ions thereof. In various embodiments, the first quadrupole selects the parent ion. The second quadrupole is maintained at a sufficiently high pressure and voltage so that multiple low energy collisions occur causing some of the ions to fragment, and the TOF mass spectrometer selects the daughter ions for detection, e.g., by monitoring the ions across a mass range which encompasses the daughter ions of interest and extracted ion chromatograms generated, by deflecting ions that appear outside of the time window of the selected daughter ions away from the detector, by time gating the detector to the arrival time window of the selected daughter ions, or combinations thereof.

The mass spectrometer system can comprise two TOF mass analyzers and an ion fragmentor (such as, for example, CID or SID). In various embodiments, the first TOF selects the parent ion (e.g., by deflecting ions that appear outside the time window of the selected parent ions away from the fragmentor) for introduction in the ion fragmentor and the second TOF mass spectrometer selects the daughter ions for detection, e.g., by monitoring the ions across a mass range which encompasses the daughter ions of interest and extracted ion chromatograms generated, by deflecting ions that appear outside of the time window of the selected daughter ions away from the detector, by time gating the detector to the arrival time window of the selected daughter ions, or combinations thereof. The TOF analyzers can be linear or reflecting analyzers.

The mass spectrometer system can comprise a tandem MS-MS instrument comprising a first field-free drift region having a timed ion selector to select a parent ion of interest, a fragmentation chamber (or ion fragmentor) to produce daughter ions, and a mass separator to transmit selected daughter ions for detection. In various embodiments, the timed ion selector comprises a pulsed ion deflector. In various embodiments, the ion deflector can be used as a pulsed ion deflector. The mass separator can comprise an ion reflector. In various embodiments, the fragmentation chamber is a collision cell designed to cause fragmentation of ions and to delay extraction. In various embodiments, the fragmentation chamber can also serve as a delayed extraction ion source for the analysis of the fragment ions by time-of-flight mass spectrometry.

In some embodiments, ionization can be used to produce structurally specific fragment ions and Q3 MRM ions. The labeling reagent can be wholly or partly contained in the structurally specific fragment ions. The method can provide both sensitivity and specificity for the Q3 MRM ions. In some embodiments, ionization can be used to produce a dominant neutral loss fragment ion which can be selected in Q3 and then fragmented to produce structurally specific ions. These fragment ions can then be used for identification and quantification in a procedure referred to as $MS^3$.

Kits

In some embodiments, the present teachings comprise kits for the analysis of the ketosterol bile acid precursors. The kit comprises one or more labels, including a set of two or more isotopically enriched standards and one or more reagents, containers, enzymes, buffers and/or instructions for use. Kits of the present teachings comprise one or more sets of supports, each support comprising a different isobaric labeling compound cleavably linked to the support through a cleavable linker. Examples of cleavable linkages comprise, but are not limited to, a chemically or photolytically cleavable linker. The supports can be reacted with different samples thereby labeling the analytes of a sample with the isobaric tag associated with the respective support. Analysis of ketosterol bile acid precursors from different samples can be contacted with different supports and thus labeled with different reporter/linker combinations.

According to various embodiments, the kit can comprise a plurality of different aminooxy tagging reagents, for example, a set of labeling reagents as described herein. The kit can be configured to analyze a plurality of different ketosterol bile acid precursors, for example, a plurality of different ketosterols, and the labeling can comprise labeling each with a plurality of different respective labeling reagents, for example, a different reagent for each different ketosterol bile acid precursor. According to various embodiments of the present teachings, a kit is provided that comprises one or more aminooxy MS tagging reagents for tagging one or more ketosterol bile acid precursors. The aminooxy MS tagging reagent can comprise a compound having one of the structures described herein.

The kit can comprise a standard comprising one or more known ketosterol bile acid precursors. The standard can comprise a known concentration of a known compound. In some embodiments, the aminooxy MS tagging reagent in the kit can comprise one or more isobaric tags from a set of isobaric tags. In some embodiments, the kit can comprise a plurality of different isobaric tags from a set of isobaric tags. In some embodiments, the aminooxy MS tagging reagent in the kit can comprise one or more permanently charged aminooxy reagents from a set of permanently charged aminooxy reagents. In some embodiments, the kit can comprise a plurality of different permanently charged aminooxy reagent tags from a set of permanently charged aminooxy reagent tags.

The kit can also comprise instructions for labeling the ketosterol bile acid precursors, for example, paper instructions or instructions formatted in an electronic file, for example, on a compact disk. The instructions can be for carrying out an assay. In some embodiments, the kit can comprise a homogeneous assay in a single container, to which only a sample need be added. Other components of the kit can comprise buffers, other reagents, one or more standards, a mixing container, one or more liquid chromatography columns, and the like.

In some embodiments, a ketosteroid analysis kit is provided that enables highly sensitive quantitation of ketosteroids from complex biological matrices, for example, detection in the range of low pg/mL concentrations.

Definitions

As used herein, the terms "diagnosis" "diagnose" and "diagnosing" refer to the process of attempting to determine or identify whether or not a subject is suffering from a given disease or condition. The term "diagnosis" does not refer to the ability to determine the presence or absence of a particular disease with 100% accuracy, or even that a given course or outcome is more likely to occur than not. Instead, the skilled artisan will understand that the term "diagnosis" refers to an increased probability that a certain disease is present in the subject. Diagnosis as used herein also includes methods for preliminary diagnosis which could be confirmed by diagnosis using other methods known in the art. Additionally, it is contemplated that the methods as described herein may be used for monitoring the progression of a condition and/or the efficacy of a therapy being used to treat a condition.

The term "screen" refers to the assay which is directed to a specific disease or clinical condition, and employs a target.

As used herein, "hydrate form" refers to any hydration state of a compound or a mixture or more than one hydration state of a compound. For example, a labeling reagent discussed herein can be a hemihydrate, a monohydrate, a dihydrate, etc. Moreover, a sample of a labeling reagent described herein can comprise monohydrate, dihydrate and hemihydrate forms.

The phrases "isobaric labels", "isobaric tags" and "isobaric labeling reagents" are used interchangeably. The phrases "set of isobaric labels", "set of isobaric tags" and "set of isobaric labeling reagents" are used interchangeably and refer to, for example, a reagents or chemical moieties where the members of the set (an individual "isobaric label," "isobaric tag," or "isobaric labeling reagent") have the identical mass but where each member of the set can produce a different daughter ion signal upon being subjected to ion fragmentation (e.g., by collision induced dissociation (CID), photoinduced dissociation (PID), etc.). A set of isobaric tags can comprise compounds of formula (I) or (II), or a salt or a hydrate form thereof. A daughter ion of an isobaric tag that can be used to distinguish between members of the set can be a reporter ion of the isobaric tag or charged analyte. A set of isobaric tags can be used to label ketosterol bile acid precursors and produced labeled compounds that are substantially chromatographically indistinguishable, but which produce signature ions following CID. The masses of the individual members of a set of mass labels can be identical or different. Where the individual isotopic substitutions are the same, the masses can be identical. Differences in selecting individual atoms for the heavy or light element incorporated into a specific label of the set can also yield mass differences based on the specific atomic weights of the isotopically enriched substituents.

As used herein, "isotopically enriched" means that a compound (e.g., labeling reagent) has been enriched synthetically with one or more heavy atom isotopes (e.g. stable isotopes including, but not limited to, Deuterium, $^{13}C$, $^{15}N$, $^{18}O$, $^{37}Cl$, or $^{81}Br$). Because isotopic enrichment is not 100% effective, there can be impurities of the compound that are of lesser states of enrichment and these will have a lower mass. Likewise, because of over-enrichment (undesired enrichment) and because of natural isotopic abundance variations, impurities of greater mass can exist.

The phrases "mass differential labels", "mass differential tags" and "mass differential labeling reagents" are used interchangeably herein. The phrases "set of mass differential labels", "set of mass differential tags" are used interchangeably and refer to, for example, a set of reagents or chemical moieties where the members of the set (i.e., an individual "mass differential label" or "mass differential tag") have substantially similar structural and chemical properties but differ in mass due to differences in heavy isotope enrichment between members of the set. Each member of the set of mass differential tags can produce a different daughter ion signal upon being subjected to ion fragmentation. Ion fragmentation can be, for example, by collisions with an inert gas (e.g., collision induced dissociation (CID), collision activated dissociation (CAD), etc.), by interaction with photons resulting in dissociation, (e.g., photoinduced dissociation (PID)), by collisions with a surface (e.g., surface induced dissociation (SID)), by interaction with an electron beam resulting in dissociation (e.g., electron induced dissociation (EID), electron capture dissociation (ECD)), thermal/black body infrared radiative dissociation (BIRD), post source decay, or combinations thereof. A daughter ion of a mass differential tag or label that can be used to distinguish between members of the set can be referred to as a reporter ion of the mass differential tag or label.

As used herein, "natural isotopic abundance" refers to the level (or distribution) of one or more isotopes found in a compound based upon the natural terrestrial prevalence of an isotope or isotopes in nature. For example, a natural compound obtained from living plant matter will typically contain about 0.6% $^{13}C$.

As used herein, the term "predominant," such as "one predominant signature ion fragment" means at least more than 50% of the ions created during the fragmentation process are the signature ions. In some embodiments, at least 60%, 70%, 80%, 90%, of the ions created during the fragmentation process are signature ion. Similarly, the terms predominantly, such as "predominantly neutral loss fragmentation" means at least more than 50% of the ions created during the fragmentation process are neutral loss fragments. In some embodiments, at least 60%, 70%, 80%, 90%, of the ions created during the fragmentation process are neutral loss fragments.

As used herein, the term "salt form" includes a salt of a compound or a mixture of salts of a compound. In addition, zwitterionic forms of a compound are also included in the term "salt form." Salts of compounds having an amine, or other basic group can be obtained, for example, by reaction with a suitable organic or inorganic acid, such as hydrogen chloride, hydrogen bromide, acetic acid, perchloric acid and the like. Compounds with a quaternary ammonium group may also contain a counteranion such as chloride, bromide, iodide, acetate, perchlorate and the like. Salts of compounds having a carboxylic acid, or other acidic functional group, can be prepared by reacting the compound with a suitable base, for example, a hydroxide base. Accordingly, salts of acidic functional groups may have a countercation, such as sodium, potassium, magnesium, calcium, etc.

As used herein, the term "unaffected" or unaffected individual, patient, or sample, refers to those individuals, patients, or samples that do not have the condition associated with 27-hydroxylase deficiency. Such individual, patient, or sample may be used for comparative samples and/or controls.

While the above description provides examples and specific details of various embodiments, it will be appreciated that some features and/or functions of the described embodiments admit to modification without departing from the scope of the described embodiments. The above description is intended to be illustrative of the teachings herein, the scope of which is limited only by the language of the claims appended hereto.

EXAMPLES

Aspects of the applicant's teachings may be further understood in light of the following examples, which should not be construed as limiting the scope of the applicant's teachings in any way.

Example 1

Extraction of Ketosteroids—Method 1

The following procedure describes the extraction of ketosterols from Dried blood, serum or plasma spot samples using isotopically enriched IS.

A sample containing 3 μL dried serum, plasma or whole blood spot (3.17 mm punch) was obtained. 50 μL (250 μg) QAO reagent in MeOH+5% acetic acid was added. 10 μL isotopically enriched internal standard (IS) (112 pg) was also added to the sample. The sample was then vortex mixed and incubated at 60 minutes at ambient temperature.

5 μL of the sample was injected for LC-ESI-MS/MS analysis. LC-MS/MS was performed using RP C8 column (Phenomenex Luna 50~4.6 mm, 5 pm at 40° C.) and API 4000™ LC/MS/MS was performed with ESI source operating in positive mode. The LC-MS/MS gradient method (8 min) was with water/acetonitrile/0.1% formic acid mobile phase.

Quantification of derivatized ketosterols was enabled by generating isotopically enriched IS.

Extraction recoveries using the above method were found to be >90% for each of 7α-cholesten-3-one, 5α-cholestan-3-one, and 4-cholesten-3-one.

Calibrators used for concentration curve: For each calibrator, 3 pL of MeOH solution which contains the desired amount of std and the internal standard was spiked onto 3.17 mm filter paper punch and let dry. DCS (Double Charcoal Stripped) serum (3 μL) was spiked on each punch disc and allowed to dry at ambient temperature. The calibrators were extracted as described above with 50 μL (250 μg) reagent in MeOH+5% acetic acid.

Figure 3:
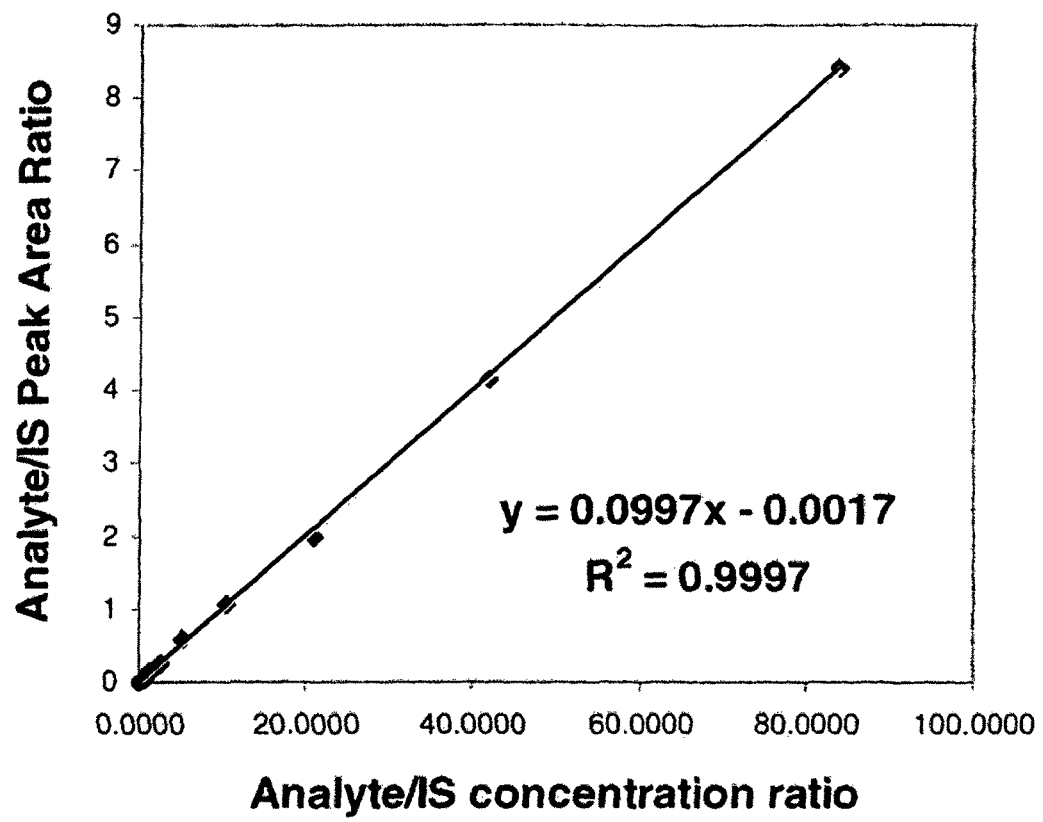
FIG. 3 provides a representative concentration curve of 7α-cholesten-3-one 1-400 ng/mL in DCS serum using this method.
Figures 4A, 4B, 4C, 4D:
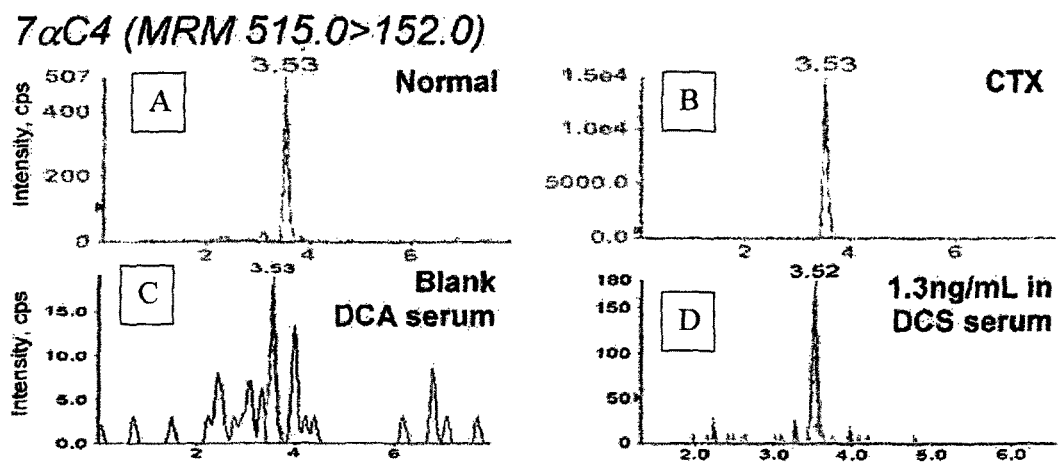
FIG. 4A-4D provides MRM data generated for QAO-tagged 7α-cholesten-3-one for dried sample spots from representative normal (FIG. 4A) and CTX (FIG. 4B) patient plasma, as well as blank DCS serum (FIG. 4C) and 1.3 ng/mL sample in DCS serum (FIG. 4D).
Figures 5A, 5B, 5C, 5D:
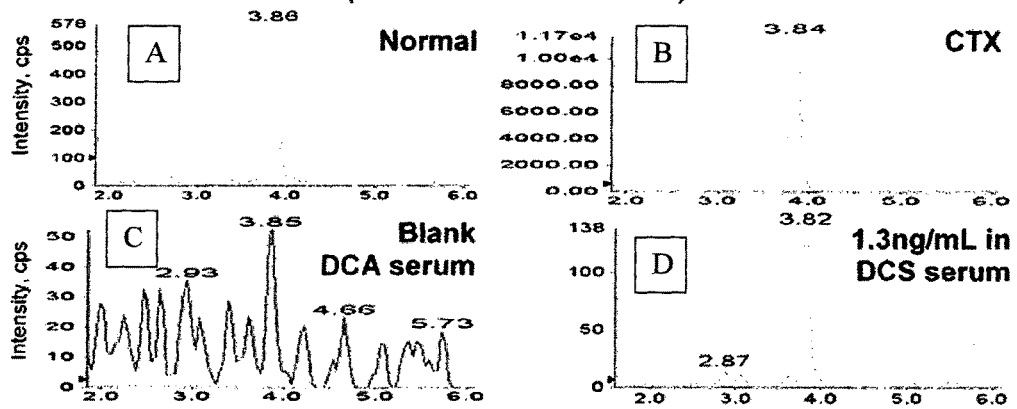
FIG. 5A-5D provides MRM data generated for QAO-tagged 4-cholesten-3-one for dried sample spots from representative normal (FIG. 5A) and CTX (FIG. 5B) patient plasma, as well as blank DCS serum (FIG. 5C) and 1.3 ng/mL sample in DCS serum (FIG. 5D).
Figures 6A, 6B, 6C, 6D:
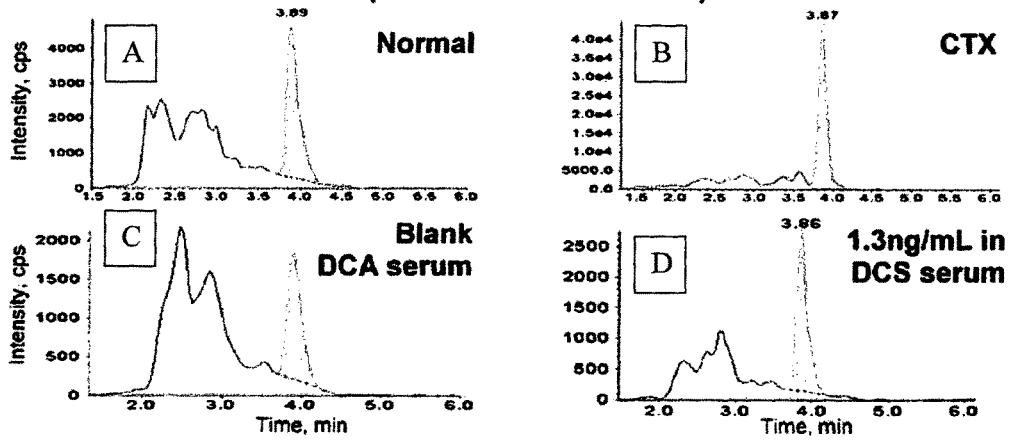
FIG. 6A-6D provides MRM data generated for QAO-tagged 5α-cholestan-3-one for dried sample spots from representative normal (FIG. 6A) and CTX (FIG. 6B) patient plasma, as well as blank DCS serum (FIG. 6C) and 1.3 ng/mL sample in DCS serum (FIG. 6D).

FIG. 3 provides a representative concentration curve of 7αC4 1-400 ng/mL in DCS serum using this method.

FIGS. 4A-4D, 5A-5D, and 6A-6D show that these QAO-tagged biomarkers co-elute as single peaks.

Table 1 provides the MS/MS conditions utilized for the analysis of 5α Cholestan-3-one, 4-Cholesen-3-one and 7α Cholestan-3-one.

TABLE 1

| Compound | MRM | DP | EP | CE | CXP |
|---|---|---|---|---|---|
| 5α Cholestan-3-one | 501.7 -> 442.6 NL | 80 | 11 | 37 | 12 |
| | 501.7 -> 93.3 Weak fragment | 80 | 11 | 87 | 12 |
| 4-Cholesen-3-one | 499.8 -> 164.2 | 60 | 10 | 64 | 12 |
| | 499.8 -> 152.1 | 60 | 10 | 64 | 12 |
| | 499.8 -> 440.8 (NL) | 60 | 10 | 30 | 12 |
| 7α Cholestan-3-one | 515.7 -> 456.8 (NL) | 85 | 12 | 38 | 14 |

TABLE 1-continued

| Compound | MRM | DP | EP | CE | CXP |
|---|---|---|---|---|---|
| | 515.7 -> 152.3 | 85 | 12 | 70 | 14 |
| | 515.7 -> 179.9 | 85 | 12 | 65 | 14 |

FIG. 7 provides QAO derivatization method performance for three different QAO-tagged ketosterols. The limit of detection, enhancement factor, linearity, dynamic range, CV, and accuracy are given. The enhancement factors after derivatization are between 275 and 2500, demonstrating a substantial improvement.

Example 2

Extraction of Ketosteroids—Method 2

The following steps describe the extraction of ketosterols from Dried blood, serum or plasma spot samples using isotopically enriched reagent.

A sample containing 3 µL dried serum, plasma or whole blood spot (3.17 mm punch) was obtained. 50 µL (250 µg) QAO reagent in MeOH+5% acetic acid was added. This mixture was vortexed and incubated 60 minutes at ambient temperature. Next, 10 µL of ketosterol analyte derivatized with isotopically enriched QAO reagent was added as IS (~112 pg).

This sample was injected for LC-ESI-MS/MS analysis (5 µL sample). LC-MS/MS was performed using RP C8 column (Phenomenex Luna 50×4.6 mm, 5 µm at 40° C.) and API 4000™ LC/MS/MS was performed with ESI source operating in positive mode. The LC-MS/MS gradient method (8 min) with water/acetonitrile/0.1% formic acid mobile phase was used.

Figure 8:
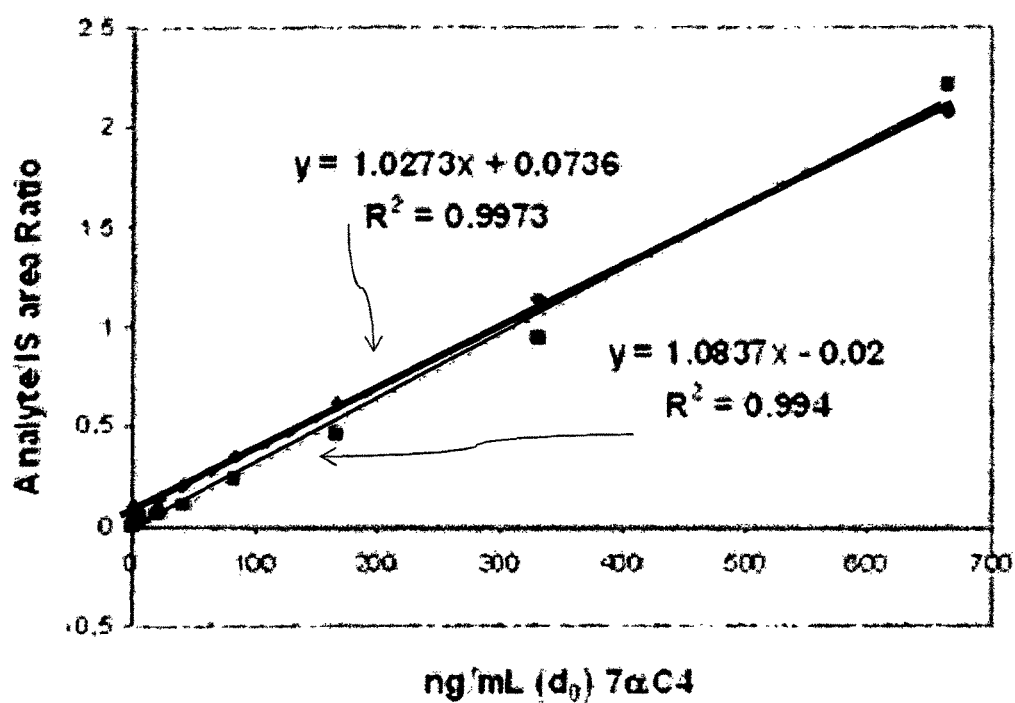
FIG. 8 is a concentration curve using d7 7αC4 as IS (squares) and deuterated reagent as IS (diamonds).

Quantification of derivatized ketosterols was enabled by generating isotopically enriched IS. For each concentration, calibration was performed. For each calibrator, 3 µL of MeOH solution which contains the desired amount of the standard was spiked with an IS onto 3.17 mm filter paper punch, and let dry. 3 µL of DCS (Double Charcoal Stripped) serum was spiked on each punch disc and let dry at ambient temperature. The calibrators were extracted as described above with 50µ>L (250 µg) reagent in MeOH+5% acetic acid. Prior to LC/MS/MS, spiked 10 µL of known concentration (112 pg) ketosterol analyte already derivatized with isotopically enriched reagent The determination of concentration as shown in the concentration curve of FIG. 6 was performed for actual samples are very close, indicating the feasibility of using deuterated reagent as IS. In FIG. 8, the reagent was spiked before LC/MS/MS.

Example 3

Extraction of Ketosteroids—Method 3

Three to 10 µL of sample which was not in a dried form were analyzed using the following method.

A sample containing 5 µL serum, plasma or whole blood spot (3.17 mm punch) was obtained. 75 µL (2.8 mglml) QAO reagent in MeOH+5% acetic acid was added. 10 µL isotopically enriched internal standard (7αC4-d7, 10 pg/µL in MeOH) was added. This sample was vortex mixed for 30 s and incubated 60-120 minutes at ambient temperature.

For LC-ESI-MS/MS analysis, 10 µL was injected. LC-MS/MS was performed using RP CS column (Phenomenex Luna 50×4.6 mm, 5 pm at 40° C.) and QTRAP 5500 LC/MS/MS was performed with ESI source operating in positive mode. A LC-MS/MS gradient method (6 min) with water/acetonitrile/0.1% formic acid mobile phase was used.

Figure 10:
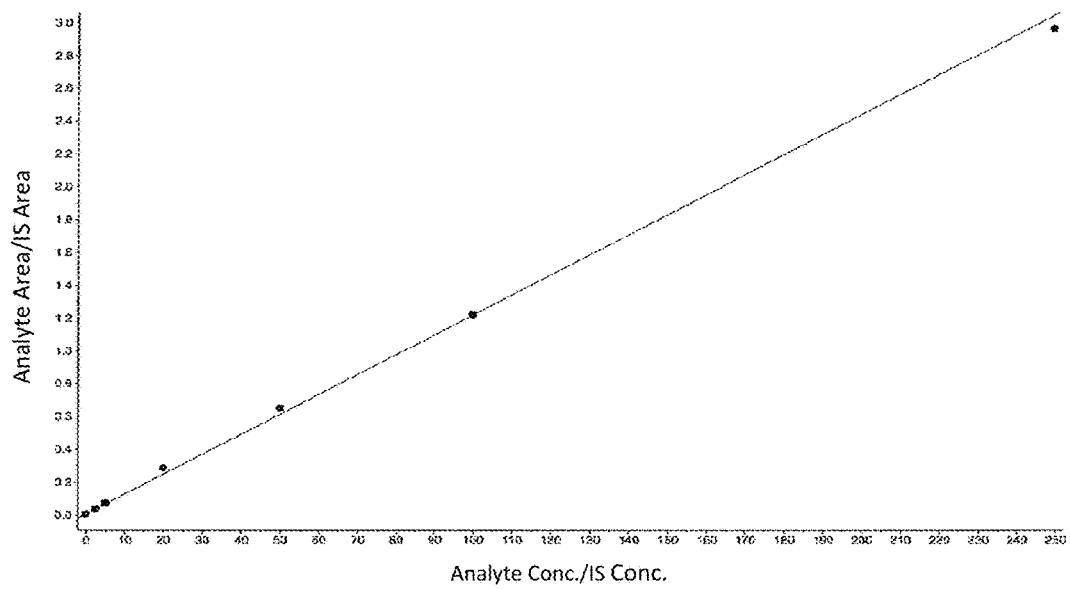
FIG. 10 is a concentration curve of 7αC4 in DCS serum using method 3.

Each calibrator is made with 5 µL DCS serum spiked with increasing concentrations of ketosterol analyte 7αC4 and IS 7αC4-d7 10 µL in MeOH solution. The calibrators as described above with 75 µL (2.8 mg/ml) reagent in MeOH+5% acetic acid were extracted. A representative concentration curve is shown in FIG. 10 for 7αC4 at concentrations between 0 and 250 nm/mL in DCS serum using Method 3.

Figures 11A, 11B, 11C, 11D, 11E, 11F:
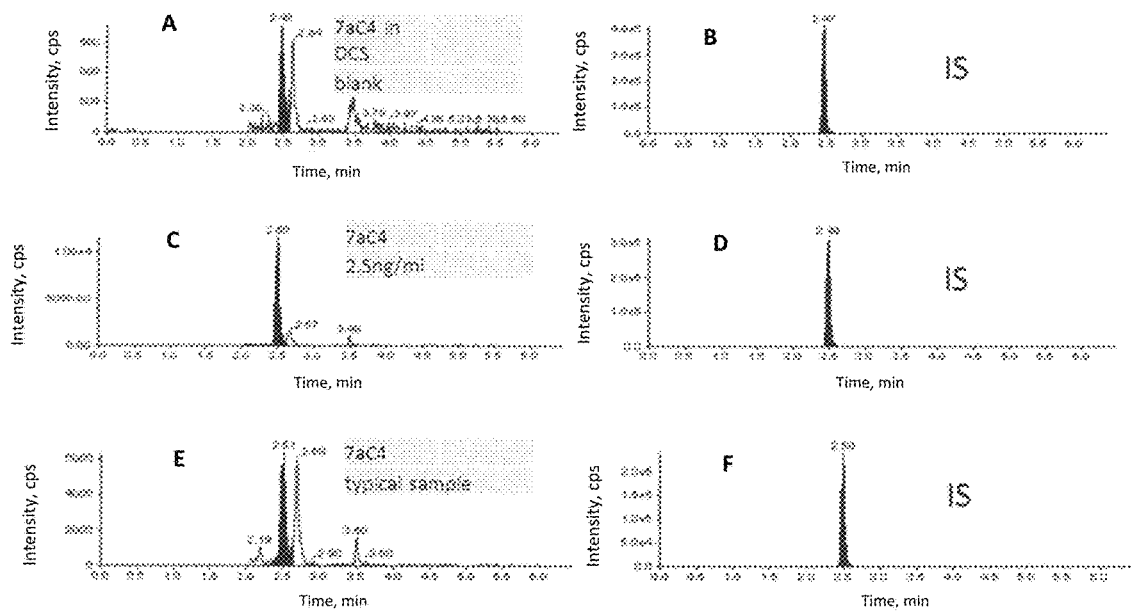
FIG. 11A-11F are representative chromatograms of blank DCS serum (some endogenous 7αC4 is present) 2.5 ng/mL std and a typical sample of a normal unaffected subject are provided where
Figure 12:
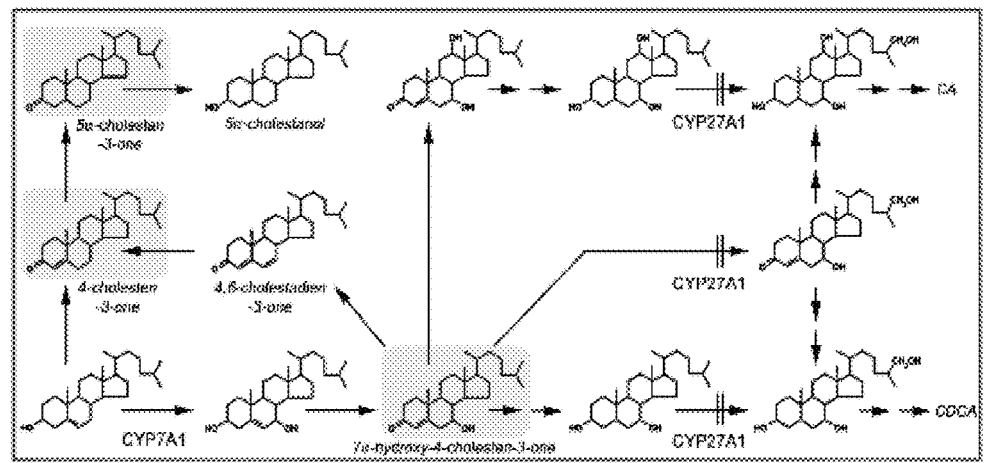
FIG. 12 Biochemical phenotype of CYP27A deficiency.

FIG. 11 provides chromatographs of typical samples for DSC serum where some endogenous 7αC4 is present.

Example 4

Extraction and Analysis of Ketosteroids

A quantitation workflow as used for the analysis of Example 4 was employed. Specifically, a plasma sample (5 µL) was combined with 50 µL QAO reagent in MeOH+5% acetic acid and 10 µL internal standard (112 pg). This mixture was vortex mixed and incubated for 1-2 hours at room temperature. 40 µL of MeOH+5% acetic acid was added. 5 µL of the sample was injected into LC-MS/MS analysis using a QTRAO 5500™.

Figures 13A, 13B:
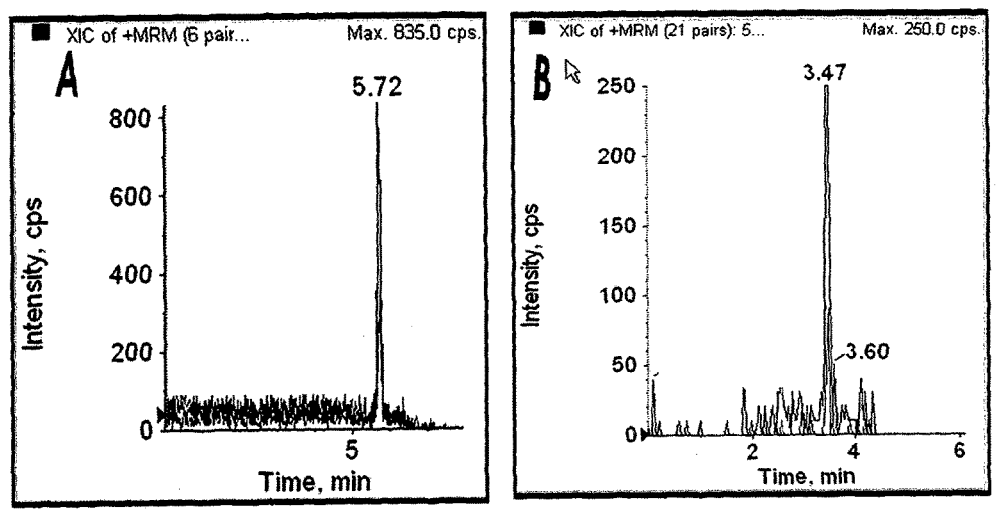
FIG. 13A is a scan of 50 pg of 7αC4 that is underivatized on a column.
FIG. 13B is a scan of 80 fg of 7αC4 that is derivatized on a column. The signal is enhanced 400-fold.
Figure 14:
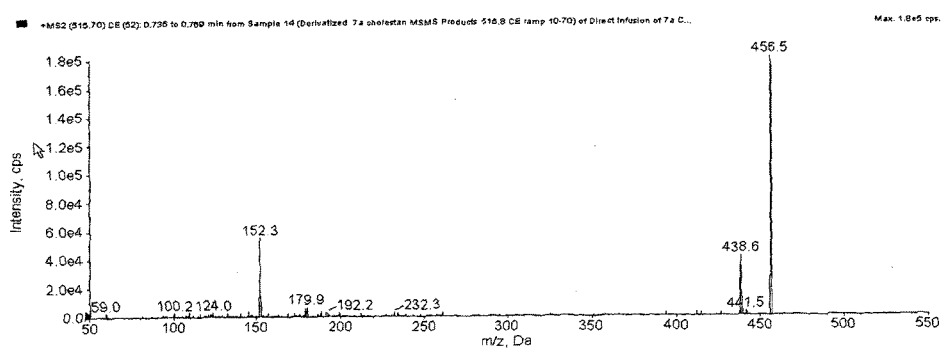
FIG. 14 is an QAO-Tagged 7αC4 Product Ion Spectrum having intensity at m/z 515.7 [M]$^+$, m/z 456.5 [M-59]$^+$, m/z 438.6 [M-59-18]$^+$, and m/z 152.3 [QAO moiety fragment]$^+$ FIGS. 15A-15C provides monitoring for QAO-tagged 7αC4 in spiked plasma calibrants where FIG. 15A provides DSC plasma at 5.0 ng/mL having a m/z transition at 515.7>152.3 FIG. 15B provides DCS plasma blank and FIG. 15C provides DCS plasma at 2.5 ng/mL.
Figures 15A, 15B, 15C:
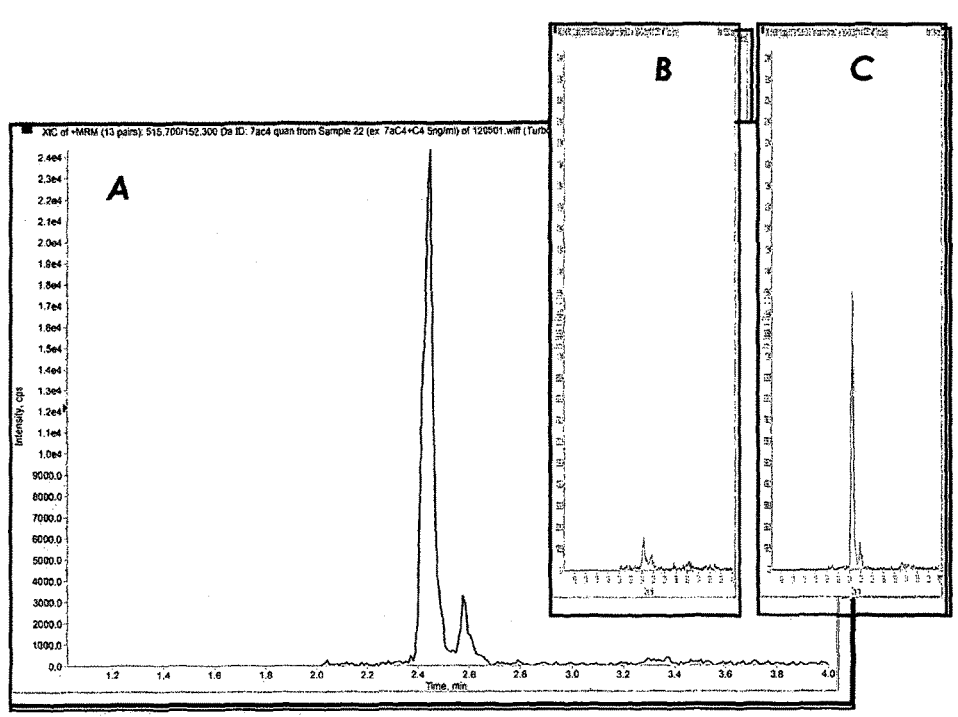
Figures 16A, 16B, 16C, 17:
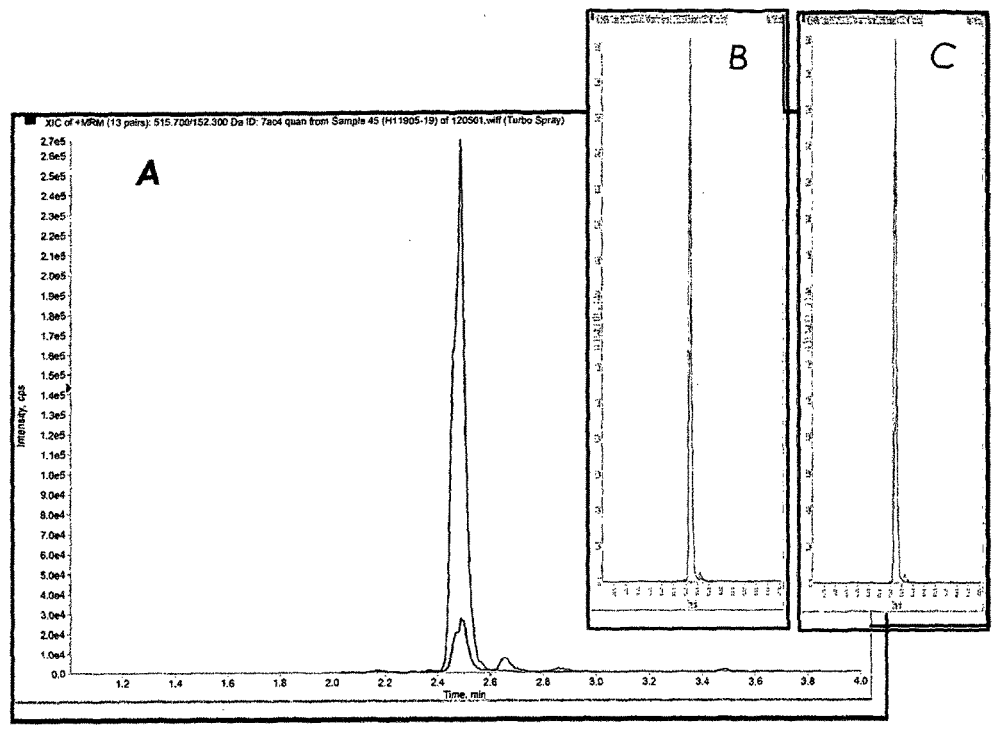
FIG. 16A-16C provides monitoring for QAO-tagged 7a C4 in plasma in a representative unaffected sample where FIG. 16A provides 7αC4-d7 derivative with a m/z transition at 518.7>152.3 (upper trace) and a 7αC4-d0 derivative with a m/z transition at 515.7>152.3 (lower trace).
FIG. 17 provides a table of 7αC4 quantitation method validation data using a QAO reagent and keto-d0 tagged 7αC4-d7 internal standard FIG. 18 provides a table of 7αC4 quantitation method validation data using a QAO reagent and keto-d3 tagged 7αC4-d0 internal standard FIG. 19 provides a table of 7αC4 concentration calculated using d7 as compared to a d3 internal standard FIG. 20A-20C provides monitoring for QAO-tagged 7α12α C4 in Plasma of a representative unaffected sample where FIG. 20A provides 7α12αC4-derivative with a m/z transition at 534.77>152.3 (upper trace) and a 7α12αC4-d0 derivative with a m/z transition at 531.7>152.3 (lower trace).
Figures 18, 19:
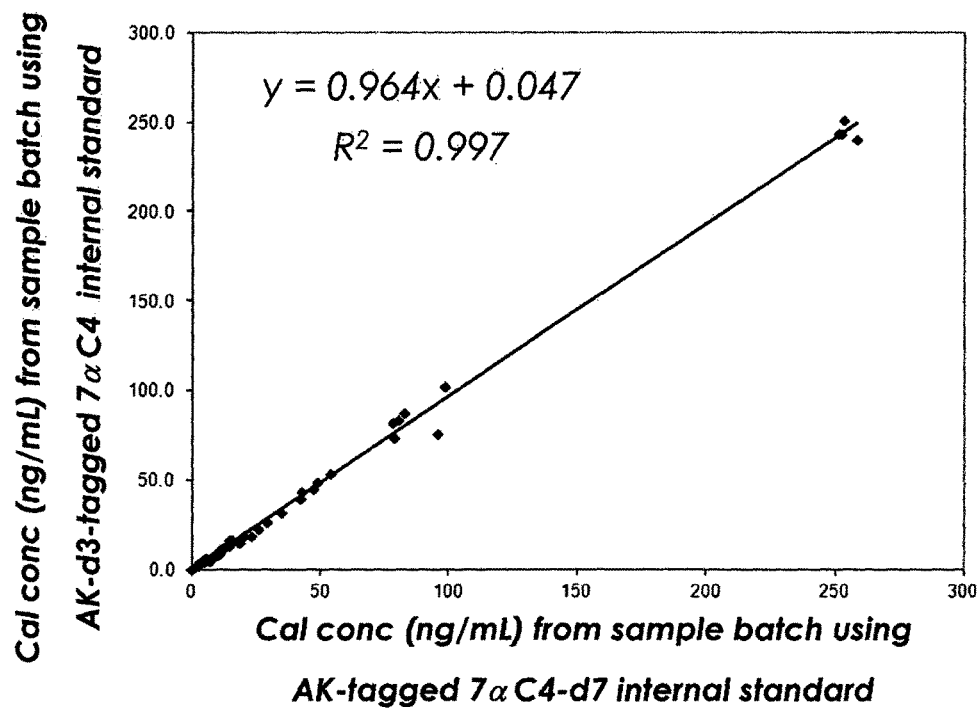
Figures 20A, 20B, 20C, 21:
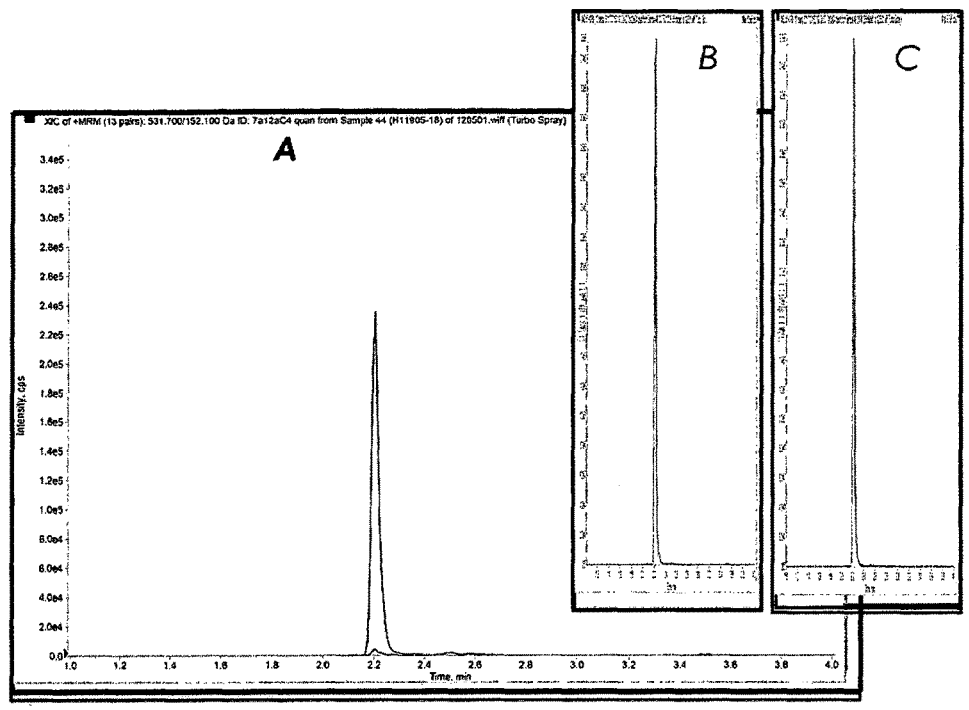
FIGS. 20B and 20C provide the CTX sample at 25-fold dilution.
FIG. 21 provides a table of 7α12αC4 quantitation method validation data using a QAO reagent and keto-d3 tagged 7α21αC4 internal standard FIG. 22 provides a table for 7αC4 and 7α12αC4 as diagnostic markers for CTX where the plasma concentration of d3-tagged internal standard FIGS. 23A-23C provides monitoring for QAO-tagged 7α12α C4 in adult DBS. A representative unaffected sample is shown in FIG. 23A where the 7α12αC4-d3 derivative with a m/z transition at 534.7>152.3 (upper trace) and the 7α12αC4-d0 derivative with a m/z transition at 531.7>152.3 (lower trace is not seen in this sample).
Figures 22, 23A, 23B, 23C:
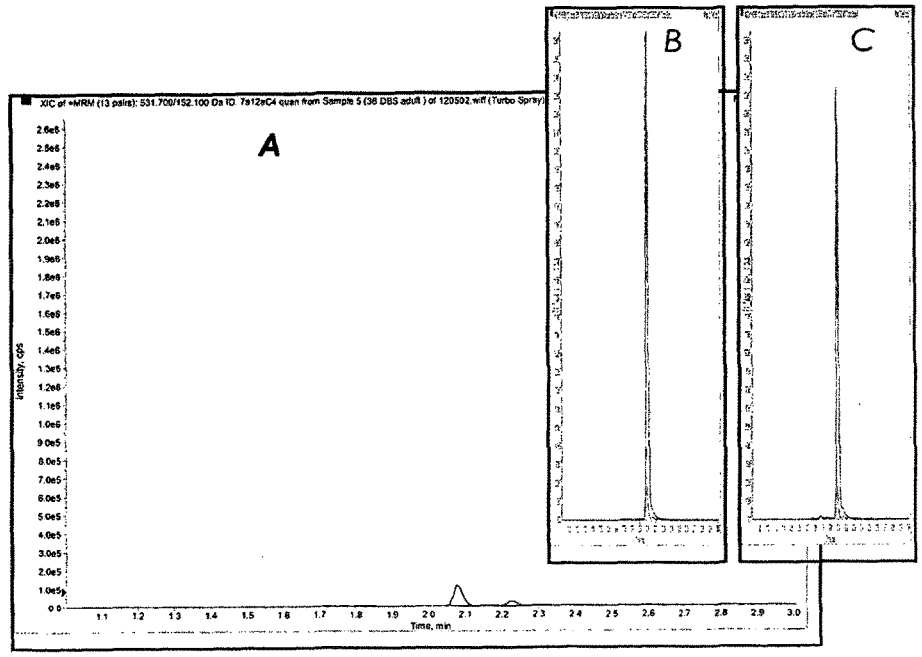
FIGS. 23B and 23C provide the CTX sample with the d0 (upper trace) and d3 (lower trace)
Figures 24A, 24B, 24C:
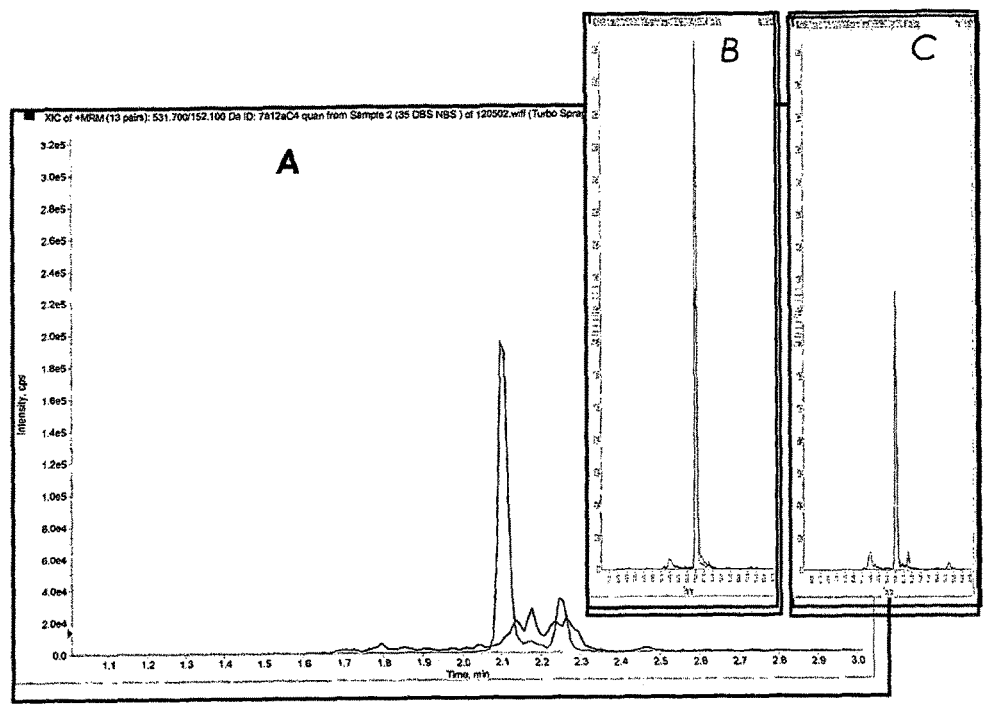
FIGS. 24A-24C provides monitoring for QAO-tagged 7α12αC4 in newborn DBS. A representative unaffected sample is shown in FIG. 24A where the 7α12αC4-d3 derivative with a m/z transition at 534.7>152.3 (upper trace) and the 7α12αC4-d0 derivative with a m/z transition at 531.7>152.3 (lower trace).

The sensitivity enhancement of this method is provided in FIG. 13, which compares scans of 50 pg of underivatized 7αC4 with 80 fg of QAO-derivatized 7αC4, where the signal is enhanced 400-fold. Ketosteroids analyzed using this workflow are described in at least some of FIGS. 14-24.

Example 5

Extraction and Analysis of 7αC4

A quantitation workflow as used for the analysis of 7αC4 was employed. Specifically, a plasma sample (5 µL) was combined with 80 µL (210 µg) QAO reagent in MeOH+5% acetic acid and 10 µL of isotopically enriched (d7) internal standard in MeOH was added. This mixture was vortex mixed and incubated for 1-2 hours at room temperature. 20 µL of IS-d3 in MeOH:H₂O was added. 5 µL of the sample was injected for LC-ESI-MS/MS analysis using a QTRAO 5500™. The analysis took 6 minutes. 7αC4 analyzed using this workflow are described in at least some of FIGS. 14-24.

All literature and similar material cited in this application, including, but not limited to, patents, patent applications, articles, books, treatises, and web pages, regardless of the format of such literature and similar materials, are expressly incorporated by reference in their entireties for all purposes. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The teachings should not be read as limited to the described order or elements unless stated to that effect. It should be understood that various changes in form and detail may be made without departing from the scope of the present teachings. By way of example, any of the disclosed method steps can be combined with any of the other disclosed steps to provide a method of analyzing ring-containing compounds in accordance with various embodiments of the present teachings. Therefore, all embodiments that come within the scope and spirit of the present teachings and equivalents thereto are claimed.

The invention claimed is:

1. A method of diagnosing or screening for 27-hydroxylase (CYP27A1) deficiency comprising:
    derivatizing an analyte containing one or more ketosterol bile acid precursors with a labeling reagent of formula (I):

where n is 2, 3, 4, 5, or 6 and Y is:

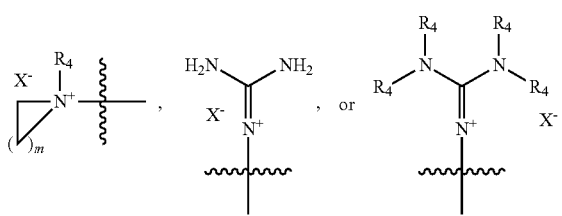

each $R_4$ is independently H or a $C_1$-$C_{18}$ alkyl which is branched or straight chain,
    m is an integer between 1 and 20, and
    X is an anion,
    or a salt or hydrate thereof, to form a labeled analyte;
    ionizing the labeled analyte;
    detecting a signature ion fragment of said labeled analyte by mass analysis, and
    comparing the intensity of said signature ion fragment to a signature ion fragment of a standard.

2. The method of claim 1, wherein said 27-hydroxylase (CYP27A1) deficiency is due to cerebrotendinous xanthomatosis (CTX).

3. The method of claim 1, wherein said 27-hydroxylase (CYP27A1) deficiency is due to Δ4-3-oxosteroid-5B reductase deficiency.

4. The method of claim 1, wherein said one or more ketosterol bile acid precursors comprises one or more of:
    7α-cholesten-3-one,
    5α-cholestan-3-one,
    4-cholesten-3-one,
    7α,12α-dihydroxy-4-cholesten-3-one,
    7α-hydroxy-5β-cholestan-3-one, and
    7α,12α-dihydroxy-5β-cholestan-3-one.

5. The method of claim 4, wherein said one or more ketosterol bile acid precursors comprises at least two of 7α-cholesten-3-one; 5α-cholestan-3-one; 4-cholesten-3-one; and 7α,12α-dihydroxy-4-cholesten-3-one.

6. The method of claim 4, wherein said derivatizing comprising derivatizing a panel of analytes comprising 7α-cholesten-3-one, and 7α,12α-dihydroxy-4-cholesten-3-one.

7. The method of claim 4, wherein said derivatizing comprising derivatizing a panel of analytes comprising 7α-cholesten-3-one, 5α-cholestan-3-one, 4-cholesten-3-one, and 7α,12α-dihydroxy-4-cholesten-3-one.

8. The method of claim 1, wherein said analyte is obtained from a biological matrix.

9. The method of claim 8, wherein said biological matrix comprises fresh blood, dried blood, serum, or plasma.

10. The method of claim 8, wherein the biological matrix has a volume of 10 μL or less.

11. The method of claim 1, wherein said signature ion fragment is a neutral loss fragment comprising a structural fragment of the analyte and the labeling reagent or a part thereof.

12. The method of claim 1, further comprising the step of derivatizing one or more standard compound(s) with a labeling reagent of formula (I) to foam a labeled standard, wherein the labeled standard is isotopically enriched, and ionizing both the labeled analyte and the labeled standard.

13. The method of claim 12, wherein said standard compound(s) comprise 7α-cholesten-3-one and 7α,12α-dihydroxy-4-cholesten-3-one.

14. The method of claim 12, wherein said detecting is performed in a single mass analysis run.

15. The method of claim 12, further comprising measuring a relative concentration of the labeled analyte relative to that of an isotopically labeled standard.

16. The method of claim 1, wherein said step of ionizing the labeled analyte is performed using a collision energy in the range of about 10 to about 130 eV.

* * * * *

UNITED STATES PATENT AND TRADEMARK OFFICE
CERTIFICATE OF CORRECTION

PATENT NO.        : 10,078,091 B2
APPLICATION NO.   : 14/401427
DATED             : September 18, 2018
INVENTOR(S)       : Andrea DeBarber et al.

Page 1 of 1

It is certified that error appears in the above-identified patent and that said Letters Patent is hereby corrected as shown below:

In the Specification

At Column 1, Lines 13-18, Delete the following:
"GOVERNMENT LICENSE RIGHTS
This invention may have been made in part with government support under OCTRI grant number 5KL2 RR024141-04 awarded by NCRR and the NCATS of the NIH. The government may have certain rights in the invention."

And replace it with the following:
-- GOVERNMENT SUPPORT
This invention was made with government support under HD061939 and RR024141 awarded by the National Institutes of Health. The government has certain rights in the invention. --

Signed and Sealed this
Twenty-second Day of October, 2019

Andrei Iancu
*Director of the United States Patent and Trademark Office*